Figure 1A:
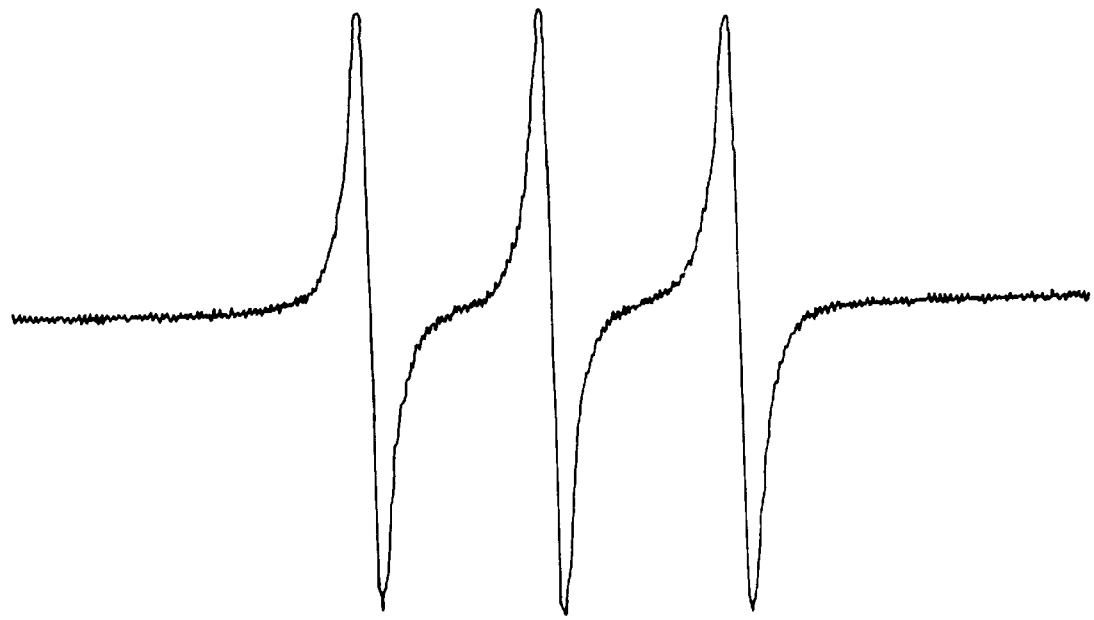

United States Patent [19]
Becker

[11] Patent Number: 6,083,988
[45] Date of Patent: Jul. 4, 2000

[54] AZULENYL NITRONE SPIN TRAPPING AGENTS, METHODS OF MAKING AND USING SAME

[76] Inventor: David Alan Becker, 2015 SW. 25th Ter., Ft. Lauderdale, Fla. 33312

[21] Appl. No.: 08/944,042

[22] Filed: Sep. 4, 1997

Related U.S. Application Data

[63] Continuation of application No. PCT/US96/18570, Nov. 15, 1996.
[60] Provisional application No. 60/006,949, Nov. 17, 1995, and provisional application No. 60/024,631, Aug. 27, 1996.

[51] Int. Cl.⁷ .............. A61K 31/435; A61K 31/275; A61K 31/165; A61K 31/15
[52] U.S. Cl. .............. 514/640; 514/12; 514/21; 514/114; 514/297; 514/510; 514/519; 514/553; 514/557; 514/561; 514/579; 514/613; 514/640; 514/644; 514/645; 514/676; 514/704; 514/740; 530/358; 530/387.1; 546/104; 546/106
[58] Field of Search .............. 514/12, 21, 114, 514/297, 510, 519, 553, 557, 561, 579, 613, 640, 644, 645, 676, 704, 740; 530/358, 387.1; 546/104, 106; 558/61, 190, 303; 560/8, 35; 562/11, 30; 564/1, 15, 123, 253, 257, 297, 298, 299, 300, 435, 440; 568/305, 423, 924, 949

[56] References Cited

U.S. PATENT DOCUMENTS

| | | | |
|---|---|---|---|
| Re. 35,112 | 12/1995 | Carney et al. | 514/400 |
| Re. 35,213 | 4/1996 | Floyd et al. | 514/400 |
| 3,509,215 | 4/1970 | Wood et al. | 260/592 |
| 4,141,995 | 2/1979 | Saunders et al. | 424/331 |
| 4,912,134 | 3/1990 | Yasunami et al. | 514/510 |
| 4,990,665 | 2/1991 | Griffing et al. | 564/265 |
| 5,025,032 | 6/1991 | Carney et al. | 514/400 |
| 5,292,746 | 3/1994 | Carr et al. | 514/278 |
| 5,405,874 | 4/1995 | Carney et al. | 514/619 |
| 5,475,032 | 12/1995 | Carney | 514/576 |
| 5,488,145 | 1/1996 | Carney | 562/62 |
| 5,508,305 | 4/1996 | Carney | 514/517 |

OTHER PUBLICATIONS

Hensley, K. et al., *NeuroReport* (1995) 6:489–492.
Brasch, R. C., *Radiology* (1983) 147:781.
Keana, J. F. and Van, N. F., *Physiol. Chem. Phys. Med. NMR* (1984) 16:477.
Socci, D. J. et al., *Brain Research* (1995) 693(1–2):88–91.
Steinberg, D., *Lancet* (1995) 346(8966):36–38.
Downs, T. R. et al., *Int'l J. Immunopharmacol.* (1995) 17(7):571–580.
Sanders, S. P. et al. *Am. J. Respir. Crit. Care Med.* (1995) 151:1725–1733.
Roza, A. M. et al., *Transplantation Proceedings* (1994) 26(2):544–545.
Bolli, R. et al. *J. Clin. Invest.* (1988) 82:476.

Oliver, C. N. et al. *Proc. Nat'l. Acad. Sci. USA* (1990) 87:5144.
Carney, J. M. et al. *Proc. Nat'l. Acad. Sci. USA* (1991) 88:3633–3636.
Floyd, R. A. *Science* (1991) 254:1597.
Floyd, R. A. and Carney, J. M. *Ann. Neurol.* (1992) 32:S22–S27.
Steinberg, D. et al. *N. Engl. J. Med.* (1989) 320:915.
Esterbauer, H. et al. *Ann. N. Y. Acad. Sci.* (1989) 570:254.
Packer, L. et al., *Biochem. Biophys. Res. Commun.* (1995) 211(3):847–849.
Chen et al. *Proc. Nat'l. Acad. Sci. USA* (1995) 92:4337–4341.
Treibs, W. et al., described *Chem. Ber.* (1959) 92:2152.
Amemiya, T. et al., in *Chem. Lett.* (1977) 587.
Beadle, J. R. et al., *J. Org. Chem.* (1984) 49:1594.
Schulz, J. B. et al., *J. Neuroscience* (1996) 16:4696–4706.
Yamashita, T. et al., *Free Radical Bio. & Med.* (1996) 21:755–761.
Uchiyama, M. et al., *Anal. Chem.* (1978) 86:271–278.
Plattner et al., *Helv. Chim. Acta* (1949) 32:2452.
Mukai, H. et al., *J. Pharmacobio–Dyn.* (1985) 8:329, 337.
*Chem. Abstr.* (1987) 106:43769.
Hafner, K. and Bernhard, C., *Angew. Chem.* (1957) 69:533.
Treibs et al. *Chem. Ber.* (1959) 92:141.
*Chem. Abstr.* (1960) 54:13090.
Anderson, A. J., Jr. et al., *J. Org. Chem.* (1965) 30:131.
Plouvier, B. et al., *Bioconjugate Chemistry* (1994) 5:475.
Huenig, S. et al., *Liebigs Ann. Chem.* (1986) 1222.
Kurokawa, S., *Bull. Chem. Soc. Jpn.* (1979) 1748.
Kitahara, Y. and Kato, T., *Bull. Chem. Soc. Jpn.* (1964) 37:859.
Repogle, L. L. et al., *J. Org. Chem.* (1967) 21:1909.
Lowry, H. O. et al., *J. Biol. Chem.* (1951) 193:265.
Kuksis, A. et al., *J. Chromatogr. Sci.* (1975) 13:423.

*Primary Examiner*—Peter O'Sullivan
*Attorney, Agent, or Firm*—Pepper Hamilton LLP

[57] ABSTRACT

The present invention relates to chromotropic nitrone spin trapping agents, methods of making these agents, compositions comprising same, and methods of their use. In particular, azulenyl nitrones of the present invention are effective agents for trapping free radical species and find use as efficient antioxidants in physicochemical and biological systems. Accordingly, the invention also relates to spin adducts formed from the combination of azulenyl nitrones with free radicals. The compounds of the present invention are readily prepared from available starting materials and find further use in assays and in a number of diagnostic, prophylactic and therapeutic applications, including but not limited to the alleviation, modulation and inhibition of the negative effects of carbon-centered or oxygen-centered radical species and other products of oxidation. Moreover, the combination adducts may be calorimetrically detected and, optionally, isolated and characterized to obtain valuable information (e.g., structural and the like) about the original reactive free radical species.

32 Claims, 1 Drawing Sheet

AZULENYL NITRONE SPIN TRAPPING AGENTS, METHODS OF MAKING AND USING SAME

REFERENCE TO RELATED APPLICATION

This Application is a continuation of International Application No. PCT/US96/18570, whose international filing date is Nov. 15, 1996, which in turn claims the benefit of U.S. Provisional Patent Application No(s). 60/006,949 and 60/024,631, filed Nov. 17, 1995 and Aug. 27, 1996 respectively, the disclosures of which Applications are incorporated by reference herein. The benefit of the filing and priority dates of the International and United States Applications is respectfully requested.

1. FIELD OF THE INVENTION

The present invention relates to chromotropic azulenyl nitrone spin trapping agents, methods of making these agents, compositions comprising same, and methods of their use. In particular, azulenyl nitrones of the present invention are effective agents for trapping and identifying free radical species and find use as efficient antioxidants in physicochemical and biological systems.

2. BACKGROUND OF THE INVENTION

2.1. General Considerations

The technique of spin trapping is an important method for garnering information on free radicals difficult or impossible to detect by direct spectroscopic observation due to their exceedingly short lifetimes and low concentrations. To date, two classes of spin trapping agents have received the most attention, namely nitroso compounds and nitrones. Of these, the latter have been more frequently used, especially in biological systems.

The most commonly cited drawbacks to the application of spin trapping agents bearing nitroso functionality are instability and toxicity. On account of these undesirable characteristics, researchers often opt for nitrone spin traps despite the fact that their nitroxide spin adducts generally provide less structural information from ESR than do those from nitroso-based spin traps. Furthermore, the nitroxides obtained from the addition of certain carbon-centered radicals (tertiary alkyl and aryl) to the most widely used nitrone spin traps alpha-phenyl-N-tert-butylnitrone (PBN), pyridine N-oxide-4-N-tert-butylnitrone (POBN) and dimethylpyrroline N-oxide (DMPO) are, due primarily to disproportionation, less persistent than those obtained from addition of such radicals to nitroso compounds.

Several groups have described the use of isotopically labeled spin traps or the application of special equipment consisting of GC/MS or HPLC-interfaced ESR spectrometers designed to detect, isolate and characterize free radical adducts of nitrone spin traps in biological systems with varied success.

2.2. Detection and Characterization of Free Radicals

Nitrones behave as spin trapping agents when a diamagnetic nitrone compound (the "spin trap") reacts with a transient free radical species (having the "spin") to provide a relatively more stable radical species (referred to as the "spin adduct"). The spin adduct may be detectable by electron paramagnetic resonance (EPR) spectroscopy if the spin adduct has a reasonable lifetime. Thus, information about the spin can be gleaned from a study of the structure and spectroscopic characteristics of the spin adduct. For example, the toxicity of synthetic beta-amyloid peptide preparations toward glutamine synthetase could be correlated with the characteristics of the EPR signal generated by the spin adduct formed from each batch of synthetic beta-amyloid peptide and the spin trap PBN. See, Hensley, K. et al., in NeuroReport (1995) 6:489–492. Beta-amyloid peptides are neurotoxic substances that are postulated to be involved in the etiology of Alzheimer's disease.

2.3. Methods of Diagnoses

Low molecular weight nitroxides are non-immunogenic. Moreover, they are typically cell permeable and can exist as a non-toxic, stable free radical capable of partitioning among various cellular compartments. Being paramagnetic, nitroxides are detectable by electron paramagnetic resonance (EPR) spectrometry and may serve as contrast agents in magnetic resonance imaging (MRI). See, Brasch, R. C., in Radiology (1983) 147:781; Keana, J. F. and Van, N. F., in Physiol. Chem. Phys. Med. NMR (1984) 16:477. Nitroxides have also been used as biophysical markers to probe cellular metabolism, oxygen level, intracellular pH, protein/lipid mobility and membrane structure. Hence, nitroxides find use in a number of diagnostic methods to determine the physiological/medical condition of a subject or the biophysical characteristics of a given sample, including samples obtained from a biological fluid.

2.4. Therapeutic Applications of Spin Trapping Agents

Free radicals and oxidative damage have been implicated in brain aging and several neurodegenerative diseases. See, Socci, D. J. et al., in Brain Research (1995) 693(1–2):88–91. Chronic treatment of aged rats with certain compounds, including the spin trapping agent alpha-phenyl N-tert-butylnitrone (PBN) and the antioxidant alpha-tocopherol (vitamin E), was found to benefit (i.e., improve) age-related changes in cognitive performance.

In vitro and in vivo evidence is mounting that the administration of antioxidants can strongly reduce the rate of progression of lesion formation associated with the process of atherosclerosis. Based on several experimental models, including low density lipoprotein (LDL)-receptor-deficient rabbits, cholesterol-fed rabbits and cholesterol-fed non-human primates, several antioxidants have manifested a 50–80% reduction in the rate of progression of lesions. The effectiveness of probucol, butylated hydroxytoluene (BHT), N,N'-diphenylphenylenediamine and vitamin E are attributed to their respective antioxidant potentials and to the proposition that oxidative modification of LDL contributes to the progression of atherosclerosis. See, Steinberg, D., in Lancet (1995) 346(8966):36–38. The one-electron oxidative potentials (vs. NHE) of vitamin E in an aqueous solution at pH 7 and 20 degrees C. is 0.48 V. The oxidative potentials of PBN, POBN and DMPO range from about 1.5–2.0 V.

Further, Downs, T. R. et al., in Int'l J. Immunopharmacol. (1995) 17(7):571–580, have shown that a cyclic nitrone antioxidant, MDL 101,002, reduces organ dysfunction and cytokine secretion induced by lipopolysaccharide (LPS) administered to rats. These authors also tested the ability of MDL 101,002 to prevent LPS-induced pulmonary edema, leukopenia and thrombocytopenia. They found that MDL 101,002 prevented pulmonary edema, partially reduced thrombocytopenia but failed to prevent leukopenia. These workers found that their results were consistent with the role that oxygen free radicals played in the development of endotoxin-induced organ dysfunction and shock. They further suggest that free radical scavengers could reduce the mortality consequent to sepsis by organ dysfunction, at least in part, through a reduction in free radical-stimulated cytokine secretion.

2.4.1. Radicals in Allergy and Allograft Rejection

Allergic reactions generate reactive oxygen species, including superoxide anions, which usher the influx of inflammatory cells to the site of allergen challenge and contribute to allergic inflammation. The inflammation may, in turn, lead to cell or tissue injury. For allergic reactions in the lung, these processes are also accompanied by increased vascular permeability and changes in airway mechanics. See, Sanders, S. P. et al. in *Am. J. Respir. Crit. Care Med.* (1995) 151:1725–1733. Thus, the administration of spin trapping agents to the site of challenge may reduce the inflammatory response and help reduce tissue or cell damage.

Separately, oxygen-derived free radicals are suspected in playing a role in cytotoxicity during episodes of allograft rejection/destruction following infiltration of the graft by mononuclear cells. The administration of radical scavengers may thus inhibit or reduce the incidence of allograft rejection. See, Roza, A. M. et al., in *Transplantation Proceedings* (1994) 26(2):544–545.

New reagents that could visually signal the formation of oxidative species would be extremely useful not only in skin tests or in cell culture but also in determining, for example, the compatibility of a patient's white blood cells with a particular kidney dialysis membrane. In vitro calorimetric assays would be of great utility.

2.5. Other Applications

PBN has been shown to offer protection in the cardiovascular disease area, in particular, by trapping free radicals generated during ischemia-reperfision-mediated injury to the heart. See, e.g., Bolli, R. et al. *J. Clin. Invest.* (1988) 82:476. The benefits of trapping free radicals generated in similar types of injury to the brain of experimental animals has also been demonstrated. See, e.g., Oliver, C. N. et al. *Proc. Nat'l. Acad. Sci. USA* (1990) 87:5144; Carney, J. M. et al. *Ibid.* (1991) 88:3636; Floyd, R. A. Science (1991) 254:1597. Oxidative damage to protein and DNA is mediated by oxygen free radical intermediates, leading to strand breaks and base modifications. Enzymes, such as glutamine synthetase, can also be inactivated by oxidative processes. Such damage can be observed, for example, in animals subjected to brain ischemnia/reperfusion injury. See, Floyd, R. A. and Carney, *J. M. Ann. Neurol.* (1992) 32:S22–S27.

Evidence is also available that PBN inhibits oxidative modification of cholesterol and triglycerides of Low Density Lipoproteins (LDL). Oxidative modification of LDL, along with lipid peroxidation and free-radical mediated reactions, is a process that is implicated in the initiation of atherosclerosis. See, e.g., Steinberg, D. et al. *N. Engl. J. Med.* (1989) 320:915; Esterbauer, H. et al. *Ann. N. Y. Acad. Sci.* (1989) 570:254.

2.5.1. Life Span Extension and Delay of Onset of Senescence

Free radicals and oxidative damage have been proposed as the underlying reasons for aging, chronic and degenerative diseases of aging, and acute clinical conditions. Daily administration by intraperitoneal injection of PBN to an aged animal model showed that PBN offered a remarkable extension of the lifespan in both male and female populations. See, Packer, L. et al., in *Biochem. Biophys. Res. Commun.* (1995) 211(3):847–849. These authors conclude that PBN could have prophylatic value against the onset of, at least, pathological senescence.

Bruce N. Ames and co-workers, in an article published in the *Proc. Nat'l. Acad. Sci. USA* (1995) 92:4337–4341, found support for the hypothesis that oxidative DNA damage contributes to replicative cessation in human diploid fibroblast cells. These workers found that senescent cells, those cells that have ceased growth in culture after a finite number of population doublings, excise from DNA four times more 8-oxoguanine per day than do early-passage young cells. Also, levels of 8-oxo-2'-deoxyguanosine in DNA of senescent cells are about a third higher than those found in DNA of young cells. Most interestingly, they found that PBN, perhaps acting as either an antioxidant or as a spin trapping agent, effectively delayed the onset of senescence and rejuvenated near senescent cells.

2.6. Applications as Food and Fuel Additives 2.6.1. Quality Evaluation of Fats

A number of factors influence fat stability and the formation of lipid oxidation products. Increased unsaturation, increased frying time, increased exposure of the oil to air and increased trace metal content will all result in decreased oxidative stability. The presence of silicones in a frying oil will cause increased oil stability by yet unknown mechanisms. Published data indicates that filtration of oils through certain active adsorbents will increase the useful frying life of an oil during actual fryer use by removal of colored materials, free fatty acids and other oxidation products.

Usually peroxides decompose at about 150° C. Therefore at frying temperatures, the accumulation of peroxides does not occur. Peroxide values usually are a measure of lipid oxidation at lower temperatures such as those used for storage of fats or a product. The relationship between storage time and peroxide value can then be used to measure quality.

The Schall oven test involves simply putting a small amount of the fat into a beaker and placing it into an oven under standardized conditions at 60° C. to oxidize the sample. Samples are then taken and peroxide values determined on them. There are many other tests available to check frying oil quality, all which purport to tell the operator when to do something with the used fat—either filter it through active filters, discard it, or dilute it with a less degraded fat. Some tests which have been used to check frying oil quality are the saponification color index, 2,6-dichloroindole phenol color test, methylene blue color test, and iodine color scale. These tests allegedly determine when the fat has gone bad and can no longer produce a high quality food product. For instance, the Rau test from E. Merck is a colormetric test kit which contains redox indicators that react with total oxidized compounds in a sample. It has a four color scale and is used for diagnoses of fat quality. The fourth color scale indicates a bad oil and the oil should be discarded. All these tests differ in reliability and may be more tedious to perform than necessary.

2.6.2. Gasoline Storage and Antioxidants

Surprisingly, difficulty in starting a lawn mower, trail bike, outboard motor, or similar infrequently used gasoline engine, is caused by "bad" petroleum. Petroleum is subject to autoxidation, like oils in foods and in the human body. When gasoline is left for any long period (e.g., a few months or more), gums are formed by the reaction of oxygen with unsaturated components of the fuel. BHT (also known as 2,6-di-tert-butyl p-cresol) is a U. S. Government approved gasoline additive that meets military requirements for gasoline stability. A half pound of BHT added to 1,100 gallons of gasoline prevents gum formation when gasoline was stored in sealed (with standard rubber washers) 5-gallon cans for periods up to two years in the Mojave desert in full sunlight, compared to a storage life of only a few months for unprotected gasoline. The amount currently recommended for military use is 1 pound BHT to 1,100 gallons of gasoline. For even longer storage, BHT, alone, may not be enough to prevent spoiling of the fuel.

Other materials besides fuels that are affected by similar aging mechanisms include plastics, rubber, paints, asphalt, roofing shingles, oils and lubricants.

Accordingly, there exists a continuing need to discover new, effective substances exhibiting free radical/spin trapping and/or antioxidant activity which are potentially useful for a wide range of analytical, preservative, diagnostic, prophylactic and therapeutic applications.

3. SUMMARY OF THE INVENTION

Accordingly, the present invention provides a new class of nitrone spin trapping agents, namely azulenyl nitrones, which can be efficiently prepared from abundant sesquiterpenes or their synthetic analog. The azulenyl nitrones of the present invention possess the unprecedented capacity to tag free radicals by yielding characteristically colored and highly visible diamagnetic (and paramagnetic) spin adducts. For example, spin trapping of 1-cyanocyclohexyl radicals (generated by thermal decomposition of the corresponding azo compound in toluene) with a green azulenyl nitrone 1 (Nu=OEt, below) produces a violet double spin adduct (via 1,3-addition of two 1-cyanocyclohexyl radicals to the nitrone moiety). The double spin adduct, by virtue of its characteristic, visible chromophore, is easily detected and purified.

The obvious green to violet chromotropism that accompanies conversion of the nitrones of the invention to commonly formed diamagnetic decomposition products of intermediate nitroxide spin adducts (which are still covalently attached to the radical units of interest) render such nitrones useful in tracking free radical residues, especially in frequently encountered cases involving fast annihilation of paramagnetic nitroxide spin adducts via either combination, disproportionation or reduction.

Vivid chromotropism (green to red) has also been observed in aerobic lipid peroxidation studies with azulenyl nitrones in corn oil and points to potential applications of these novel nitrones as indicators of oxidative stress in lipids or as preservatives in such lipids or other compositions susceptible to oxidative breakdown, including other foodstuffs and fuels. The azulenyl nitrones of the invention are also useful for alleviating a host of ill effects caused generally by reactive free radicals or oxidative processes in biological systems.

Therefore, it is an objective of the present invention to provide a compound of the general formula, below,

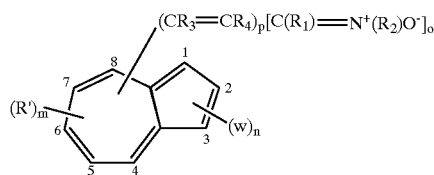

in which $R_1$ may be a hydrogen, a linear or branched alkyl group comprising 1–6 carbon atoms, or an aryl group comprising 6–10 carbon atoms; $R_2$ may be a linear or branched alkyl group comprising 1–6 carbon atoms, or an aryl group comprising 6–10 carbon atoms; $R_3$ may be a hydrogen, or a linear or branched allyl group comprising 1–6 carbon atoms; $R_4$ may be a hydrogen, or a linear or branched allyl group comprising 1–6 carbon atoms; R' may be a linear or branched alkyl group comprising 1–6 carbon atoms; W may be a linear or branched alkyl group comprising 1–6 carbon atoms, an aryl group comprising 6–10 carbon atoms, or an electron-withdrawing group; n may be 0, 1, or 2 (if n is 2, each W may be the same as or different from one another); m may be 0, 1, 2, or 3 (if m is 2 or 3, each R' may be the same as or different from one another); o may be 1 or 2 (if o is 2, each $R_1$ and $R_2$ may be the same as or different from one another); p may be 0, 1, or 2 (if p is 2, each $R_3$ and $R_4$ may be the same as or different from one another) or a salt thereof.

In specific embodiments of the invention, a compound is contemplated in which o is 1, p is 0, n is 1, m 1 or 2, or in which the groups $R_1$, $R_3$, and $R_4$ are all hydrogen, in which at least one R' is a methyl, ethyl, or isopropyl group, or in which the group $R_2$ is a tert-butyl group. Of particular interest are compounds in which W is an electron-withdrawing group.

In other embodiments, the compound of interest bears the group $(CR_3=CR_4)_pC(R_1)=N^+(R_2)O^-$ at the 1-position of the azulene ring system when the group W is at the 3-position. In still others, m is 2 and the groups R' are at the 4- and 7-positions. Further, the group W may be a carboxylic acid, carboxylic acid ester, sulfonic acid, sulfonic acid ester, ketone, halogen, cyano, nitro, nitroso, aldehyde, phosphoric acid, phosphoric acid ester, sulfoxide, sulfone, or a salt thereof. In preferred cases, W is a carboxylic acid, sulfonic acid, or their salts, or a trifluoroacetyl group.

In terms of stereochemistry, the $R_3$ and $R_4$ groups of the general formula, as well as the $R_1$ and $R_2$ groups of the general formula, may be cis or trans to one another. Preferably, the $R_3$ and $R_4$ groups are trans to each other and the $R_1$ and $R_2$ groups are cis to one another. The $R_5$ and $R_6$ groups of the general formula, may be cis or trans to one another, preferably, trans to each other.

Certain compounds are preferred, including 2-methyl[1-(3-carboxylic acid-7-isopropyl-4-methyl) azulenylmethylene]-2-propanamine N-oxide; 2-methyl[1-(3-carboethoxy-7-isopropyl-4-methyl)azulenylmethylene]-2-propanamine N-oxide; 2-methyl[1-(3-sulfonic acid-7-isopropyl-4-methyl)azulenyhmethylene]-2-propanamine N-oxide; 2-methyl[1-(3-methylsulfonyl-7-isopropyl-4-methyl)azulenylmethylene]-2-propanamine N-oxide; 1,3-bis(2-methyl-2-propanamine N-oxide)azulenyldimethylene; and 1,3-bis(2-methyl-2-propanamine N-oxide)-7-isopropyl-4-methylazalenyl-dimethylene. Each compound of the invention includes its acid, ester, amide, salt, or crystalline form, as appropriate.

The invention also contemplates a variety of methods, including but not limited to, a method of trapping a reactive free radical comprising providing a compound of the invention and allowing the compound to combine with a reactive free radical to provide an adduct comprising the free radical and the compound, a method of detecting oxidation products in a medium comprising combining or contacting a compound of the invention with a medium and detecting the presence of an adduct or an end-product thereof in the resulting mitre, a method of alleviating the ill effects of a pathologic condition mediated or initiated by a reactive free radical comprising administering an effective amount of the compound of the invention to a subject in need thereof. Still other methods include, but are not limited to, methods of alleviating, ameliorating, treating, preventing, managing, or inhibiting the negative effects of ischemia, reperfusion injury, trauma (particularly head or brain trauma), acute respiratory distress syndrome, neurological (especially cerebral) disorders, Alzheimer's disease, stroke, Parkinson's disease, Huntington's disease, Lou Gehrig's disease, Wilson's disease, aging, senescence, apoptosis, inflammation and the like.

The invention further contemplates compositions comprising a compound of the invention and an appropriate carrier, especially compositions having pharmaceutical, dermatological, cosmetic, or industrial applications.

It should also be apparent that the invention is further directed to a spin adduct comprising a combination product of an azulenyl nitrone and a free radical.

Likewise, it is also an object of the invention to provide a process for making an azulenyl nitrone comprising: (a) providing an azllene; (b) introducing a acyl group to the azulene at a position that is to bear a nitrone group; and (c) converting the acyl group to a nitrone group to provide an azulenyl nitrone.

Other objects of the present invention, including compositions and methods of using the azulenyl nitrones of the invention will be apparent to one of ordinary skill considering the detailed descriptions provided herein.

4. BRIEF DESCRIPTION OF THE FIGURE

Figure 1B:
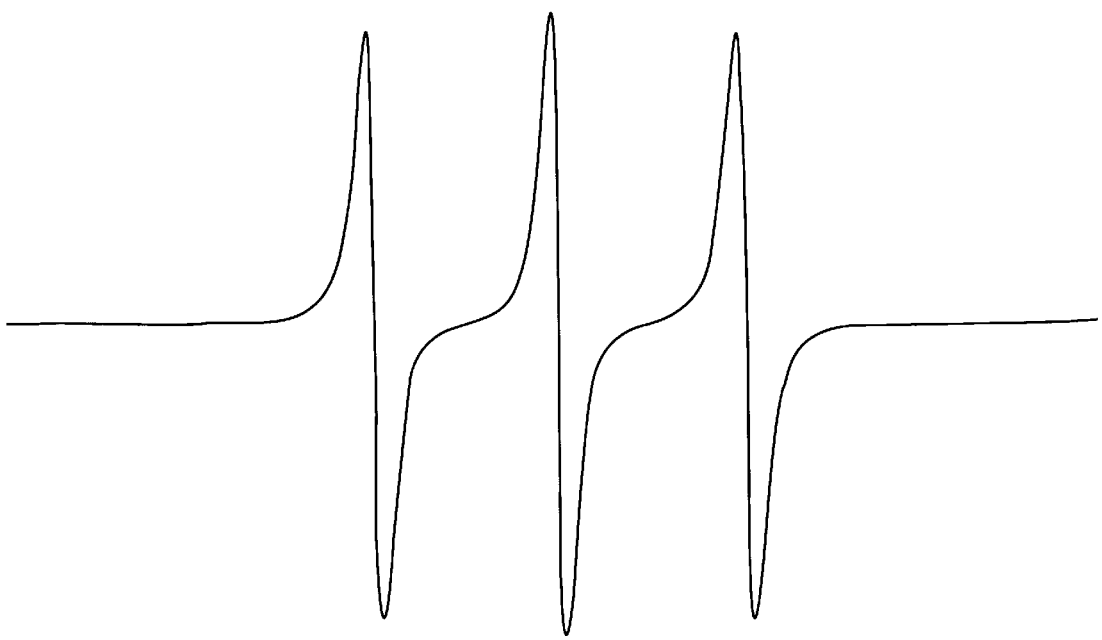

FIGS. 1A and 1B illustrates the three-line ESR signal generated by the nitroxide spin adduct formed by the combination of azulenyl nitrone, 1 (Nu=OEt) and the free radical derived from the thermolysis of AMVN azulenyl nitrone, Compound 1.

5. DETAILED DESCRIPTION OF THE PREFERRED EMBODIMENTS

Herein is reported a new and simple colorimetric approach to the detection, isolation and analysis of free radical adducts of nitrones employing the novel nitrone spin trapping agents, such as 1 (Nu=OEt), which are easily obtained from azulene and its derivatives, including the abundant sesquiterpene, guaiazulene.

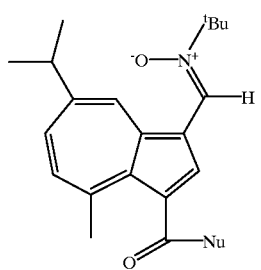

1

Of particular importance regarding spin trapping with the azulenyl nitrones of the present invention is their capacity to tag free radicals by yielding characteristically colored and highly visible diamagnetic (and paramagnetic) spin adducts. Thus, nitrones, such as 1 (Nu=OEt), or any of the other nitrones contemplated herein, provide the potential to implicate the intermediacy and establish the identity of free radicals in situations in which presently available ESR detection/isolation technology may fail.

Albeit considerably more persistent than most free radicals, nitroxides are nevertheless often subject to the usual free radical destruction processes of combination, disproportionation, and oxidation/reduction, yielding diamagnetic products. The rapid formation of diamagnetic spin adducts in traditional spin trapping experiments is an unwanted occurrence which can constitute a serious obstacle, because once such products are formed in biological systems employing conventional nitrone spin traps, they are lost amidst a vast number of diverse diamagnetic molecules.

The ability to easily locate diamagnetic spin adducts in complex mixtures offers an appealing alternative should one be faced with technical difficulties often encountered while attempting to isolate nitroxides resulting from conventional nitrone spin traps before they decay into diamagnetic species. In spin trapping with the compounds of the present invention, the characteristic chromophore of the diamagnetic spin adducts arising from nitroxides via combination, disproportionation or reduction, while crucially different from the chromophore of the azulenyl nitrone, is in fact the same as that of the initially formed ESR-detectable nitroxide spin adducts. Therefore, this characteristic chromophore should also expedite the purification (and subsequent structure determination) of these paramagnetic species from reaction mixtures amenable to nitroxide longevity.

Even though nitroxides possess a visible chromophore of their own, their characteristic red color is due to an absorption with a very low extinction coefficient centered around 460 nm. For example, the visible absorption spectrum in hexane for di-t-butylnitroxide shows a maximum at 465 nm with log e=0.95. The extinction coefficient for the absorption giving rise to the color of the diamagnetic azulene-containing spin adducts described herein is between one to two orders of magnitude greater. See, Smith, P. A. S. *Open-Chain Nitrogen Compozinds,* W. A. Benjamin, Inc., New York, 1965, Vol. 2, p. 105 and references cited therein for additional discussions on nitroxide absorption spectra.

5.1. Preparation of Azulenyl Nitrones

Azulenyl nitrones of the present invention are prepared readily from a variety of available starting materials. For example, the azulenyl nitrone, 1 (Nu=OEt) a stable green solid (mp 43–45° C.), is readily prepared in three steps from guaiazulene (Scheme I, below). Exposure of guaiazulene to oxalyl bromide in ether at room temperature according to the method of Treibs, W. et al., described in Chem. Ber. (1959) 92:2152, yields acyl bromide 2, which is directly esterified with EtOH to provide the violet ethyl ester 3 in 80% yield. Oxidation of 3 with two equivalents of DDQ in aqueous acetonitile at room temperature in analogy to the method of Takase (See, Amemiya, T. et al., in *Chem. Lett.* (1977) 587) affords a 74% yield of red aldehyde 4.

Condensation of 4 with N-tertbutylhydroxylamine hydrochloride in pyridine at 95° C. provides 1 (Nu=OEt) in nearly quantitative yield. Spectral data for 1 (Nu=OEt): $^1$H NMR (300 MHz, CDCl$_3$): 9.74(s, 1H), 8.36(s, 1H), 8.17(s, 1H), 7.54(d, J=11 Hz, 1H), 7.43(d, J=11 Hz, 1H), 4.37(q, J=7 Hz, 2H), 3.17(m, 1H), 2.97(s, 3H), 1.71(s, 9H), and 1.38–1.43 (m, 9H). $^{13}$C NMR (75.4 MHz, CDCl$_3$): 167.2, 148.7, 145.8, 141.3, 141.0, 137.7, 136.8, 132.7, 132.5, 123.0, 120.7, 117.1, 69.6, 60.8, 38.3, 28.4, 27.9, 24.4, and 14.4. IR (neat): 3135, 2965, 2930, 2905, 2870, 1715, 1580, 1560, 1460, 1335, 1300, 1245, 1195, 1150, 1105, 1040, 920 cm$^{-1}$. UV-VIS max (hexane): 313 nm ($\epsilon$=26,071), 358 (15,526), 417 (8,390), and 588 (532). Exact Mass (FABMS, NBA); Calculated for C$_{22}$H$_{30}$NO$_3$ (M$^+$+1): 356.2226. Found: 356.2230.

SCHEME 1

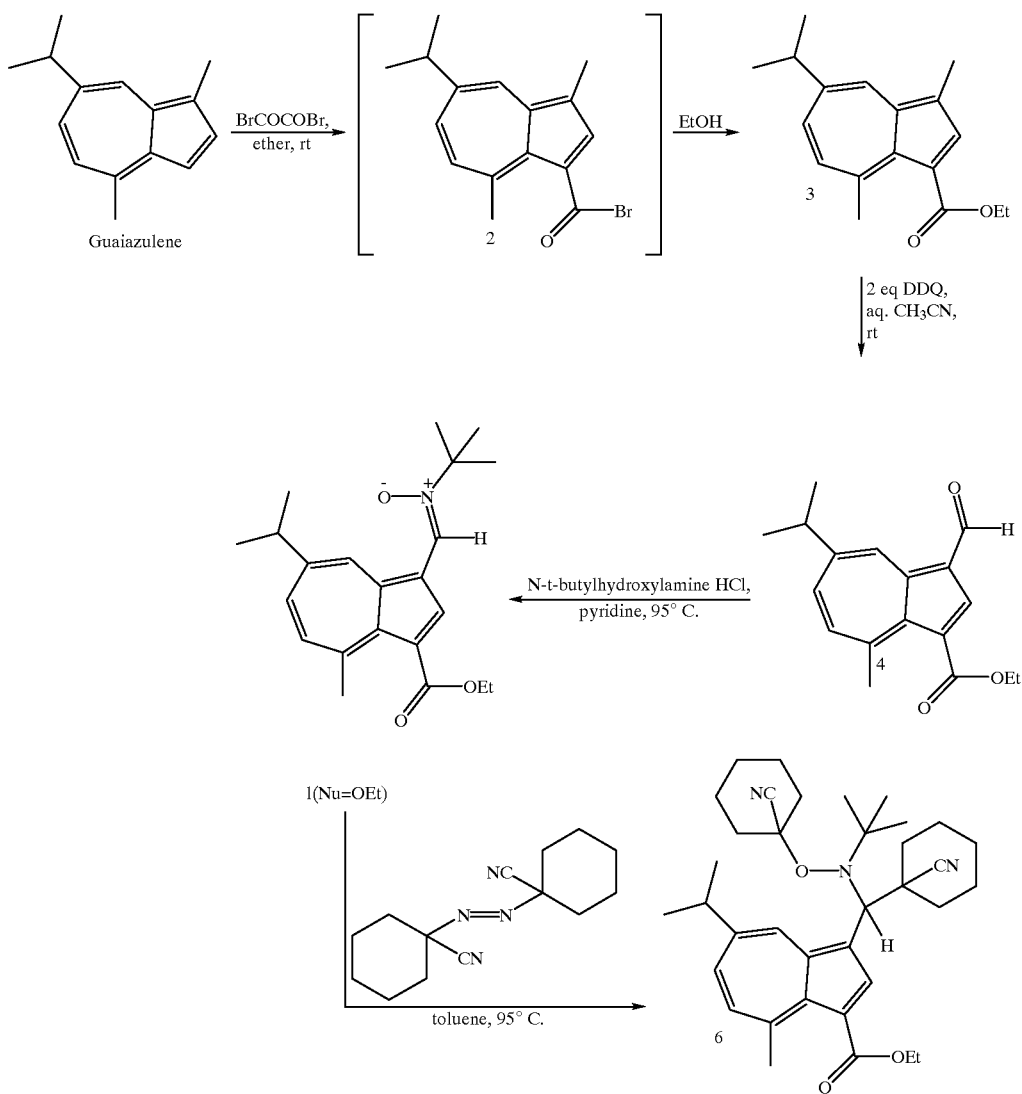

5.1.1. Preparation of Bis-Nitronyl Azulene

Bis-nitrones are also readily prepared by the methods of the invention. In particular, the bis-nitronyl azulene 34, a water soluble dark green crystalline material (mp 211–212° C.), is readily prepared from the bis-aldehyde, 1,3-azulenedicarboxaldehyde. The bis-aldehyde is prepared according to the method of Hafaer, K. and Bernhard, C., *Annalen* (1959) 625:108. The bis-nitrone is prepared as follows.

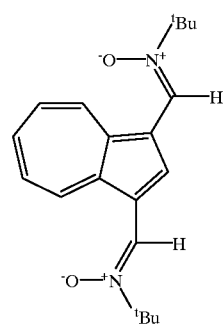

34

1,3-Azulenedicarboxaldehyde (600 mg) is dissolved in 6.5 ml of pyridine. Magnesium sulfate (1200 mg) and N-tert-butylhydroxylammne hydrochloride (1638 mg,) is added to the solution,. The mixture is heated wit stirring to 95° C. under nitrogen and is stirred for 13 hours. Upon cooling to rt, the reaction mixture is poured into a separator flinnel containing 60 ml of $CHCl_3$ and 60 ml of sat aq. $NaHCO_3$. The aqueous layer is separated and washed with three 30 ml portions of $CHCl_3$. The combined organc layers are dried over anhydrous $MgSO_4$, filtered, and evaporated to give the bis-nitrone 34 (940 mg, 89% yield) as dark green crystals. Oxidation potential equals 0.72 V vs SCE. $^1$H NMR ($CDCl_3$): 10.35 (s, 1H), 8.65 (d, 2H, J=10 Hz) 8.11 (s, 2H), 7.68 (t, 1H, J=10 Hz), 7.32 (t, 2H, J=10 Hz), 1.67 (s, 18H). $^{13}$C NMR ($CDCl_3$): 139.9, 135.0, 134.2, 125.8, 125.6, 123.2, 120.5, 69.8, 28.4. IR (thin film): 3052, 2972, 1644, 1564, 1452, 1404, 1356, 1261, 1196, 1124, 1052, and 892 $cm^{-1}$.

5.1.2. Preparation of Conjugated Azulenyl Nitrones

Coupling azulenyl nitrones such that they are in electronic conjugation reduces their oxidation potential and thus forms a more reactive spin trapping agent. Electronically conjugated azulenyl nitrones are prepared from a conjugated azulenyl chain. Conjugated azulene chains are made by coupling azulene carboxaldehydes that, in turn, are prepared by a variety of methods. Bis-aldehydes are prepared as described in Section 5.1.1. Azulenes with a single aldehyde substituent is prepared similarly.

For example, guiazulene is converted to its aldehyde by treatment with phosphorous oxychloride ($POCl_3$) in an excess of dimethylformamide to provide guiazulene carboxaldehyde. The guiazulene carboxaldehyde is dimerized in high yield to an alkene-linked conjugated, unsaturated system by treatment with titanium trichloride. The coupled product is treated with DDQ, then with magnesium sulfate and N-tert-butylhydroxylamine hydrochloride, as described in Section 5.1, to generate the 1,2-bis(azulenyl nitrone) ethylene. A general formula is as follows:

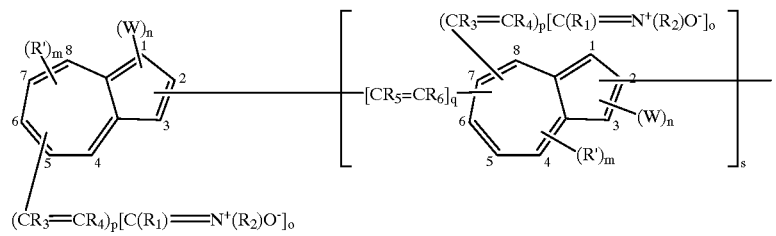

in which s can be 0 or greater, preferably 1, 2, 3, 4, 5, or up to 100. It should be apparent to those of ordinary skill, that a dimer can be prepared or a polymer having three, four, five, or many more azulenyl units, by the methods disclosed in the present invention.

Using the methods herein, any number of azulenyl nitrones can be prepared. Accordingly, the following representative compounds, including their salts (especially their alkali and alkaline-earth metal salts or their acetic and hydrochloride acid addition salts) are obtained by the methods of the present invention:

1  2-methyl[1-(3-carboethoxy-7-isopropyl-4-methyl) azulenylmethylene]-2-propanamine N-oxide; having an IUPAC name of (Z)-3-[[1,1-dimethylethyl)oxidoimino] methyl]-8-methyl-5-(1-methylethyl)-1-azulenecarboxylic acid, ethyl ester (CAS Registry No. 174355-72-7)

2  2-methyl[1-(3-dimethylamido-7-isopropyl-4-methyl) azulenylmethylene]-2-propanamine N-oxide

3  2-methyl[1-(3-formyl-7-isopropyl-4-methyl) azulenylmethylene]-2-propanamine N-oxide

4  2-methyl[1-(3-carboxylic acid-7-isopropyl-4-methyl) azulenylmethylene]-2-propanamine N-oxide, sodium salt

5  2-methyl[1-(3-trifluoroacetyl-7-isopropenyl-4-methyl) azulenylmethylene]-2-propanamine N-oxide

6  2-methyl[1-(3-acyl-7-isopropyl4-methyl)azulenyl-methylene]-2-propanamine N-oxide, spermine conjugate

7  2-methyl[1-(3-diethylamido-7-isopropyl4-methyl) azulenylmethylene]-2-propanamine N-oxide

8  2-methyl[1-(3-acyl-7-isopropyl-4-methyl)azulenyl-methylene]-2-propanamine N-oxide, N-methyl(D) glutamine conjugate

9  2-methyl[1-(3-octadecylamido-7-isopropyl-4-methyl) azulenylmethylene]-2-propanamine N-oxide

10  2-methyl[1-(3-acyl-7-isopropyl-4-methyl)azulenyl-methylene]-2-propanamine N-oxide, sphingosine conjugate

11  2-methyl[1-(3-acyl-7-isopropyl-4-methyl)azulenyl-methylene]-2-propanamine N-oxide, polylysine conjugate

12  2-methyl[1-(3-acyl-7-isopropyl-4-methyl)azulenyl-methylene]-2-propanamine N-oxide, $(dG)_{10}$ conjugate

13  2-methyl[1-(3-acyl-7-isopropyl-4-methyl)azulenyl-methylene]-2-propanamine N-oxide, anti-bovine IgG (mouse) mAB conjugate

14  2-methyl[1-(3-acyl-7-isopropyl-4-methyl)azulenyl-methylene]-2-propanamine N-oxide, N-(3-aminopropyl)-9 acridinamine conjugate

15  2-methyl[1-(3-acyl-7-isopropyl-4-methyl)azulenyl-methylene]-2-propanamine N-oxide, histone type II-AS conjugate

16  2-methyl[1-(3-N-t-butyinitronyl)-7-isopropyl-4-methyl) azulenylmethylene]-2-propanarnine N-oxide

17  2-methyl[1-(7-isopropenyl-4-methyl) azulenylmethylene]-2-propanamine N-oxide

18 2-methyl[1-azulenylhethylene]-2-propanamine N-oxide

19  2-methyl[6-azulenylmethylene]-2-propanamine N-oxide

20 2-methyl[4-azulenylmethylene]-2-propanarine N-oxide

21 2-methyl[4-(1-methyl-7-isopropyl)azulenylmethylene]-2-propanamine N-oxide

22  2-methyl[6-(1,4-dimethyl-7-isopropyl)azulenyl-methylene]-2-propanamine N-oxide

23  2-methyl[1-(3-carboethoxy-7-isopropyl-4-methyl) azulenylmethylene]-2-propanamine N-oxide

24  2-methyl[1-(3-cyano-7-isopropyl-4-methyl)azulenyi-methylene]-2-propanamine N-oxide

25  2-methyl[1-(3-methylsulfonyl-7-isopropyl-4-methyl) azulenylmethylene]-2-propanarnine N-oxide

26  2-methyl[1-(3-sulfonic acid-7-isopropyl-4-methyl) azulenylmethylene]-2-propanamine N-oxide, sodium salt

27  2-methyl[1-(3-dimnethylphosphonato-7-isopropyl-4-methyl)azulenylmethylene]-2-propanamine N-oxide

28 2-methyl[1-(3-phosphondioxy-7-isopropyl-4-methyl) azulenylmethylene]-2-propanamine N-oxide, disodium salt

29 2-methyl[1-(3-nitro-7-isopropyl-4-methyl) azulenylmethylene]-2-propanamine N-oxide

30 2-methyl[1-(3-carboethoxy-7-isopropyl4-methyl) azulenylpropenylene]-2-propanamine N-oxide

31 2-methyl[1-(7-acetyl-4-methyl)azulenylmethylene]-2-propanamine N-oxide

32 [1-(3-carboethoxy-7-isopropyl-4-methyl)azulenyl-methylene]benzenamine N-oxide

33 2-methyl[1-(7-isopropyl-4-methyl)azulenylmethylene]-2-propanamnine N-oxide

34 1,3-bis(2-methyl-2-propanarnine N-oxide) azulenyldimethylene

35 1,2-bis(azulenyl nitrone)ethyene

Doubtless, other azulenyl nitrones, especially various metal, ammonium, or acid addition salts, not specifically listed above, will be apparent to those of ordinary skill in view of the present disclosure. Such other azulenyl nitrones are considered to fall within the scope of the present invention, however.

5.2. Characteristics of the Azulenyl Nitrones 5.2.1. Adduct Formed with Free Radical Species The obvious chromotropism that accompanies conversion of nitrone spin traps, such as 1 (Nu=OEt), to diamagnetic free radical adducts arising via either combination, disproportionation, or reduction of intermediate nitroxides is unprecedented and may render them useful in tracking free radical residues in frequently encountered cases involving fast annihilation of nitroxide spin adducts via any of the aforementioned processes.

Thus, when an emerald green solution of azulenyl nitrone 1 (Nu=OEt) in toluene (60 mM) is heated to 95° C. in the presence of azo compound 5 under argon (See, Scheme I, above), TLC analysis of the progress of the reaction reveals the formation of a violet product of lower polarity than 1 (Nu=OEt). When the reaction mixture is poured onto a flash chromatography column containing chloroform-saturated silica gel and eluted with chloroform, a violet band descends and is easily collected. Further purification by preparative TLC (chloroform) affords the violet double spin adduct 6. Spectral data for 6: $^1$H NMR (300 MHz, CDCl$_3$): 8.74(s, 1H), 8.20(s, 1H), 7.57(d, J=11 Hz, 1H), 7.36(d, J=11 Hz, 1H), 4.57(s, 1H), 4.39(q, J=7 Hz, 2H), 3.13, (m,1H), 3.02(s, 3H), 1.53–2.78(m, 20H), 1.35–1.49(m, 9H), and 1.14(s, 9H). IR (neat): 2960, 2940, 2860, 2220, 2200, 1705, 1415, 1260, 1195, 1095, 1040, and 800 cm$^{-1}$. UV-VIS max (hexane): 301 nm ($\epsilon$=10,209), 351 (2,097), 370 (2,558), and 548 (198). Exact Mass (FABMS, NBA); Calculated for $C_{36}H_{50}N_3O_3$ (M$^+$+1): 572.3852. Found: 572.3853.

5.2.2. Competitive Spin Trapping Behavior

An inspection of the $^1$H NMR spectrum of the reaction mixture formed in a competitive spin trapping experiment entailing therrnolysis (95° C., 6 h) of a toluene solution containing 100 mM concentrations of 1 (Nu=OEt), PBN, and azo compound 5 indicates that, relative to PBN, nitrone 1 (Nu=OEt) produces a roughly equal amount of the corresponding double spin adduct. It should be noted that the one election oxidation potential of 1 (Nu=OEt) is much lower (0.48-D.52V) than that of PBN. That double spin adduct 6 is not an artifact produced via a mechanism involving the intermediacy of carbanionic species is supported by the absence of the compound (1-cyanocyclohexyl)-diphenylmethanol in the reaction mixture (as determined by $^1$H NMR and TLC comparison with an authentic sample) when the thermolysis is conducted in the presence of an equimolar concentration of benzophenone. In toluene solution, benzophenone is preferentially attacked by carbanions (e.g., organolithium derivatives) in the presence of equimolar concentrations of nitrone 1 (Nu=OEt).

Results concerning the use of 1 (Nu=OEt) in trapping other types of carbon-centered radicals (such as aryl radicals) have likewise been encouraging. For example, on the basis of $^1$H NMR analysis of the spectra of the violet and green products formed when nitrone 1 (Nu=OEt, 10 mg, 100 mM in benzene) is subjected to conditions for the generation of the 4-bromophenyl radical (according to the Gokel modification of the Gomberg-Bachmann reaction), their structures have been assigned as the corresponding hydroxylamine (violet) and nitrone (green) resulting from disproportionation of the expected intermediate nitroxide radical. That these products are also formed in 9:1 benzene:t-BuOH argues strongly against their being artifacts formed via the involvement of aryl carbanion intermediates. See, e.g., Beadle, J. R. et al., in J. Org. Chem. (1984) 49:1594.

5.2.3. Oxidation and Chromotropism

Chromotropism has also been observed in experiments employing nitrone spin trap 1 (Nu=OEt), and like compounds, in lipid peroxidation studies. Dissolution of 10 mg of 1 (Nu=OEt) in 50 ml of corn oil and bubbling of air through the resulting green oil at 90° C. for 9.5 hr yields a bright red oil from which, after partitioning between hexane and acetonitrile, one can isolate from the acetonitrile layer 300 mg of crude reddish material, which when subjected to TLC analysis, shows the presence of a major red product. This red product has been identified as aldehyde 4 (See, Scheme I, above) and is postulated to arise from decomposition of a spin adduct between nitrone 1 (Nu=OEt) and an oxygen-centered radical. Nitrone 1 (Nu=OEt, 5.65×10$^4$M) is unchanged in 98:1:1 EtOAc:HOAc:water after 10 hours at 90° C. in a sealed tube. The green nitrone 1, then, on reaction with a peroxide radical (e.g., hydroperoxide HOO·, or alkylperoxide ROO·) gives rise to a combination product that is violet (presumably, a nitroxide adduct), which on hydrolysis (or some other decomposition reaction, such as hyrogen abstraction, disproportionation, fragmentation and the like) gives rise to an end product that is red, corresponding to the aldehye 4 (1-(3-carboxylic acid-7-isopropyl-4-methyl) azulenyl carboxaldehyde, ethyl ester).

The difference in color between the nitrone and the aldehyde is reflected in the differences in the UV/VIS absorption spectra of the two compounds in alcoholic solvent, in which the nitrone has a strong absorption around 305 nm and the aldehyde a sharp peak around 255 nm. Both compounds have medium absorption peaks around 390 nm.

The electrochemical oxidation of the of the azulenyl nitrone into the aldehyde appears to take place around 600 mV in an aqueous environment. The redox reaction in acetonitrile is reversible, indicating an oxidation potential of 0.84 V v. SCE for the nitrone 1.

Further, when a control experiment is conducted with argon bubbling in the presence or absence of water, this red product is not detected and the recovered green oil contains no azulenic products other than the starting azulenyl nitrone. Similarly, no observable chromotropism and complete recovery of the unreacted nitrone is the outcome of an aerobic control experiment substituting chlorobenzene, a solvent devoid of easily abstractable hydrogen atoms, in place of corn oil. This data strongly suggests that the observed change in color from green to red is instigated by addition to nitrone 1 Nu=OEt) of free radicals formed by autoxidation, presumably involving linoleic acid subunits of the corn oil glycerides. The application of these nitrones as indicators of oxidative stress in lipids is thus demonstrated.

Moreover, by virtue of the presence of acyl bromide intermediate 2 (See, Scheme I, above) in the synthesis of these nitrones, one can envision making a wide range of easily prepared derivatives whose physical properties can be modulated by judicious choice of a nucleophile (alcohol, amine, etc.) to employ in acylation reactions with 2. Lipophilic or hydrophilic side chains at this position should drastically influence solubility properties and the exploitation of this electrophilic site for the preparation of bioconjugates may afford interesting spin traps with efficient targeting capacities.

The free radical scavenging and antioxidant properties of nitrones have been recent topics fostering intense activity in the biological/pharmacological arena. Much evidence points to the role of free radical damage in the etiology of a number of pathological conditions such as atherosclerosis, Alzheimer disease, cancer, ischemia-reperfusion injury, and senescence.

5.2.4. Azulenyl Nitrones on Solid Supports

Since azulenyl nitrones exhibit chromotropism, these compounds are useful as indicators of free radicals reagents in a gas, liquid, or solid medium. In this example, the azulenynl nitrones are bound to a solid support (e.g., via reactive functional groups, such as hydroxyl groups, on the solid support). The solid support bound azulenyl nitrone is generally insoluble in the medium to be tested or monitored for the presence of free radicals. Hence, this method of the detection of free radicals can be performed without contaminating the medium. The azulenyl nitrones are bound to a solid support, which may be in the form of beads, solid strip, paper, or any form suitable for the testing conditions. Furthermore, the reaction product generated between the azulenyl nitrone and any free radical can be isolated by simply filtering the solid support. The reaction product can then be isolated from the solid support, free of the medium, by hydrolyzing or breaking the bond binding the azulenyl nitrone (actually the spin adduct) to the solid support. This method permits the identification of the free radicals that are present in the medium being tested and which give rise to the formation of the spin adduct.

For example, polyvinyl acetate beads are partially hydrolyzed, thereby exposing hydroxyl groups on the surface capable of bonding to the azulenyl nitrone (e.g., the acid form). The amount of hydrolysis of the beads and the concentration of azulenyl nitrone substituents are varied to adjust the sensitivity of the beads to free radicals. The beads are immersed in vegetable oil. The mixture is heated and exposed to air bubbling through the mixture resulting in a visible color change. The beads are removed from the vegetable oil, thereby removing any contaminant. The reaction product generated with the azulenyl nitrone and radical is isolated by hydrolyzing the product with a base. The unbound reaction product can then be analyzed by conventional methods.

5.3. In Vitro and In Vivo Studies Using Azulenyl Nitrones 5.3.1. Protective Effect Against Oxidative Damage To study the protective effects of azulenyl nitrones, such as 1 (Nu=OEt), against oxidative damage induced by various modalities, the clonogenic cell survival is a reliable end point. A diverse group of cells ranging from prokaryotes to mammalian cells can be used. Preferably, because of their rapid doubling time and high plating efficiency, Chinese hamster V79 lung fibroblasts are chosen, which are grown in sterile Ham's F12 medium supplemented with 10% fetal calf serum with glutamine and without sodium bicarbonate (Hyclone Laboratories, Logan, Utah), penicillin at 0.14 mg/ml, and streptomycin at 0.2 mg/ml.

Drug treatment or high-energy irradiation is performed in the presence or absence of varying concentrations (0.1–100 mM) of the azulenyl nitrones of the present invention. In a typical experiment, $5 \times 10^5$ cells in 5 ml medium are plated into a 100-mm petri dish and incubated (95% air/5% $CO_2$, by volume) for 16 hr at 37° C. Following cell adherence to the plates and exponential growth, 10 mM 1 (Nu=OEt) and 0–1.2 mM $H_2O_2$ are added. After 1 hr the cells are rinsed, treated with 0.03% trypsin, counted, and divided into dishes to be incubated for macroscopic colony formation. After 7 days the cells are fixed with methanol/acetic acid (3:1, v/v), stained with 0.3% crystal violet, rinsed, and air-dried, and the colonies containing over 50 cells are counted. In this way the dose-dependent protective effect of azulenyl nitrones of the invention are evaluated.

5.3.2. Brain Antioxidant Activity

The brain antioxidant activity of azulenyl nitrones are studied using two groups of animals: (i) young adult male gerbils (3–4 months of age) and (ii) aged, retired, male breeder gerbils (18–20 months of age). Such gerbils may obtained from Tumblebrook Farms (West Brookfield, Mass.). The gerbils are housed three in a cage in standard rodent cages. Animals are maintained in an animal facility under a 12-hr light-dark cycle. All experiments are conducted during the light phase of the cycle. Food and water are available ad lithium throughout the day.

Young adult male (3–4 months of age) and retired male breeder gerbils (18–20 months of age) are assigned to separate groups of 18 gerbils each. One group of young adult and aged animals is assigned to the vehicle (saline) control group, and the other groups receive the sodium salt of Compound #4(Nu=OH). Animals are given intraperitoneal injections twice daily (8:00 a.m. and 8:00 p.m.) for a period of 14 consecutive days. The sodium salt of Compound # 4(Nu=OH) is dissolved in neutral saline and administered at a dose of 1–50 mg, preferably 30 mg/kg/injection (3.0 mg/ml). In subsequent studies, substantially lower doses (1–10 mg/kg/injection) are used with comparable results.

At the end of the 14 days, the animals are given an additional day of no injections to allow for the elimination of any residual azulenyl nitrone prior to testing. After the 24 hour washout period, the gerbils are tested for radial arm maze performance.

An eight-arm, or like, radial maze is used for testing patrolling behavior performance. The gerbils are placed one at a time in the central compartment of the sunburst maze. When the doors to the arms are raised, each gerbil is free to explore the maze. Reentry into an arm more than once before exploring all eight arms is considered an error. Arm entry is registered electronically. Animals have 15 min to explore the maze.

Normal young adult gerbils make between 4 and 5 errors, while aged gerbils make 9–11 errors. After 14 days of treatment with the sodium salt of Compound #4(Nu=OH), the young adult gerbils make the same number of errors as the control group In contrast, when nitrone-treated aged gerbils are tested they make significantly fewer errors. In fact, the aged gerbils surprisingly make about the same number of errors as do the young adult gerbils.

5.3.3. In Vivo Diagnostic Applications

Azulenyl nitrones are detectable by UV/VIS spectroscopy and HPLC. Upon reaction with free radicals and subsequent breakdown of the adduct, the nitrones generate the corresponding azulenyl aldehydes. Such aldehydes arise from the breakdown of spin adducts formed with oxygen-centered free radicals. The aldehydes are, in turn, also detectable by UV/VIS spectroscopy. When a subject is dosed with nitrones and subsequently treated in some fashion (e.g., ischemia and/or reperfusion) to cause the formation of free radicals in some part of the subjects anatomy, the amount of free radicals induced in the subject can be gauged by measuring the amount of aldehyde produced. (The nitrone should be recovered unchanged if no oxidation reaction takes place.) Thus, the aldehyde to nitrone ratio can be determined in the subject's biological fluids and/or tissue samples (e.g., in the blood, cerebral, or cardiovascular tissue). In this fashion, azulenyl nitrones are used to gauge the relative levels of reactive free radical production in various locations and/or fluids of the subject. Such analytical techniques can also demonstrate that the azulenyl nitrones of the present invention are able to penetrate certain barriers that are present in the animal or human anatomy, such as the blood-brain barrier, or whether these compounds prefer to remain or localize in certain tissues (e.g., hippocampus) or fluids (e.g., plasma) after different modes of administration, e.g., iv, ip, po, topical, intramucal, opthalmic, etc.

5.3.4. In Vivo Neuroprotective Applications

Because azulenyl nitrones react with free radicals, physiological events and/or pathological conditions that lead to the formation of free radicals and which thereby cause damage to the subject suffering from such event or condition can be prevented, inhibited, or alleviated by the administration of azulenyl nitrones. A method of determining the effectiveness of azulenyl nitrones as a neuro- or cerebroprotectant involves the administration of azulenyl nitrones to test animals, including rodents such as gerbils or mice. An ischemic episode is then induced in the test animal. For example, a useful stroke model is provided by subjecting the test animal to a bilateral carotid occlusion (BCO), which reduces the flow of blood to the brain and can result in brain damage and/or tissue infarction. The blood and brains of the BCO-treated rodents are analyzed to determine the relative amounts of azulenyl nitrone and aldehyde. The ratio of the aldehyde to nitrone concentrations is compared to that found in sham rodents, which were not subjected to one of the oxygen free radical producing procedure. The results indicate that the ratio is higher (i.e., that more aldehyde is observed) in the test rodents versus the sham rodents, indicating that the administration of azulenyl nitrones to these rodents proceeds to a redox reaction/combination, which affords the end product, aldehyde.

The administration of the azulenyl nitrones of the invention to the test rodents affords neuroprotection because control animals receiving saline (or phenyl t-butyl nitrone or PBN) exhibit impaired motor function and/or behavior compared to the test animals. Moreover, analysis of brain slices and heart slices indicates a reduction in the cerebral and myocardial infarct volume, respectively, relative to saline control or animals receiving PBN.

5.3.5. In Vitro Protection

The protective effects of azulenyl nitrones are investigated by subjecting a cell culture to compounds known to induce death in the cells. The nitrone is administered in varying doses to determine the amount needed to inhibit or prevent cell death. By this method, the efficacy of azulenyl nitrones is determined and found to be largely dose dependent.

As an example, cerebella granular cells (neuronal cells) are treated with a sublethal dose of a toxic agent, e.g., cis-platin, buthionine sulfoximine, or peroxynitrite. The nitrone is either added prior to or after treatment with the toxic agent. Azulenyl nitrone 1 is found to be a neuroprotectant in a dose dependent manner, preventing or reducing neural cell death in doses of between 10 to 100 $\mu$M.

Similarly, it is found that the azulenyl nitrones of the invention, when added to cell cultures, particularly prokaryotic, eukaryotic, and especially mammalian cells, extend the period of cell viability relative to a control cell culture that received no azulenyl nitrone. Hence, the invention inhibits cell apoptosis. (See, e.g., Schulz, J. B. et al., in *J. Neuroscience* (1996) 16:4696–4706.). Similar results are obtained with a variety of neuroprotective cell toxicity assays.

5.3.6. Protection of Liver Oxidation

The protective effect of azulenyl nitrones on the formation of oxidative damage in liver DNA and on lipid peroxidation is demonstrated by experiments using Long-Evans Cinnamon (LEC) rats. See,.e.g., Yamashita, T. et al., in *Free Radical Bio. & Med.* (1996) 21:755–761. These rats belong to a new mutant strain with hereditary hepatitis and are used as models for treating Wilson's disease. LEC rats die of fllninant hepatitis within about a week of the development of severe jaundice without intervention.

In the experiment, the rats are maintained under conventional conditions. Food and water are available ad lithium throughout the day. Two sets of female rats are used between the ages of 10 to 30 months old. To one set is subcutaneously administered the azulenyl nitrone 34 in a vegetable oil composition, while the second set is subcutaneously administered vegetable oil alone. The amount administered corresponds to about 100 mg/kg of active ingredient and is administered twice daily for about 15 to 30 weeks. The liver tissue of the rats is removed and measured for lipid peroxidation according to the method of Uchiyama, M. et al., in *Anal. Chem.* (1978) 86:271–278. In this way the dose-dependent protective effect of azulenyl nitrones of the invention are evaluated and shown to be remarkable.

5.4. Pharmaceutical Compositions Comprising the Azulenyl Nitrone Compounds of the Present Invention As should be apparent, the present invention contemplates compositions comprising the azulenyl nitrone compounds disclosed herein. Preferably, these compositions include pharmaceutical compositions comprising a therapeutically effective amount of an azulenyl nitrone compound along with a pharmaceutically acceptable carrier.

As used herein, the term "pharmaceutically acceptable" carrier means a non-toxic, inert solid, semi-solid liquid filler, diluent, encapsulating material or formulation auxiliary of any type. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and conventional antioxidants can also be present in the composition, according to the judgement of the formulator. Examples of pharmaceutically acceptable conventional antioxidants include water soluble antioxidants such as ascorbic acid, cysteine hydrochloride, sodium bisulfite, sodium metabisulfite, sodium sulfite, and the like; oil soluble antioxidants such as ascorbyl pahmitate, butylated hydroxyanisole (BHA), butylated hydroxytoluene (BHT), lecithin, propyl gallate, alphatocopherol and the like: and the metal chelating agents such as citric acid, ethylenediamine tetraacetic acid (EDTA), sorbitol, tartaric acid, phosphoric acid and the like.

By a "therapeutically effective amount" of an azulenyl nitrone compound, such as 1 (Nu=OEt) or the sodium salt of Compound #4(Nu=OH), is meant a sufficient amount of the compound to alleviate, modulate, or inhibit the negative or, otherwise, ill effects of free radical species and/or associated medical disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the medical disorder being treated and the severity of the medical disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidently with the specific compound employed; and like factors well known in the medical arts.

The total daily dose of the azulenyl nitrone compounds of the present invention administered to a human subject in single or in divided doses can be in amounts, for example, from 0.01 to 35 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the compound(s) of this invention per day in multiple doses or in a single dose offrom 1 mg, 5 mg, 10 mg, 100 mg, 500 mg or 1000 mg. A submilligram dose may also be appropriate, namely, about 0.1–0.9 mg, preferably, about 0.3, about 0.5, or about 0.7 mg.

The compounds of the present invention may be administered alone or in combination or in concurrent therapy with other agents that exhibit antioxidant activity, such as PBN.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsiying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a therapeutic agent, it is often desirable to slow the absorption of a therapeutic agent from subcutaneous or intramuscular injection. The most common way to accomplish this is to inject a suspension of crystalline or amorphous material with poor water solubility. The rate of absorption of the therapeutic agent becomes dependent on the rate of dissolution of the therapeutic agent which is, in turn, dependent on the physical state of the therapeutic agent, for example, the crystal size and the crystalline form. Another approach to delaying absorption of a therapeutic agent is to administer the therapeutic agent as a solution or suspension in oil.

Injectable depot forms can also be made by forming microcapsule matrices of therapeutic agent and biodegradable polymers such as polylactide-polyglycoside. Depending on the ratio of therapeutic agent to polymer and the composition of the polymer, the rate of therapeutic agent release can be controlled. Examples of other biodegradable polymers include poly-orthoesters and polyanhydrides. The depot injectables can also be made by entrapping the therapeutic agent in liposomes or microemulsions which are compatible with body tissues.

Suppositories for rectal administration of the therapeutic agent can be prepared by mixing the therapeutic agent with a suitable nonirritating excipient such as cocoa butter and polyethylene glycol which are solid at ordinary temperature but liquid at the rectal temperature and will, therefore, melt in the rectum and release the therapeutic agent.

Solid dosage forms for oral administration may include capsules, tablets, pills, powders, prills and granules. In such solid dosage forms the active spin trapping compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active nitrone compounds can also be in microencapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a nitrone compound of this invention, for either therapeutic or cosmetic applications, further include ointments, pastes, creams, lotions, gels, powders, solutions, sprays, inhalants (e.g., through the oral cavity or intranasally) or patches. The active nitrone component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active nitrone compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

Accordingly, the present invention is useful in the treatment or alleviation of disease, especially those disorders related to oxidized species, free radicals, or products of oxidation, including products of polymorphonuclear leukocyte oxidative burst. Such medical conditions may be characterized by inflammation, rheumatoid arthritis, autoimmune disease, flu-like symptoms, decreased cognitive ability, cardiovascular disease, atherosclerosis, respiratory discomfort and the like, which can be reduced by the administration of an effective amount of the azulenyl nitrone compounds of the present invention.

Reactive free radicals in living tissue are believed to promote heart disease, cancer, Alzheimer's disease, Parkinson's disease, ainyotrophic lateral sclerosis (or ALS), rheumatoid arthritis and even antineoplastic (anticancer, antitumor) induced cardiotoxicity. There exist many mechanisms that induce the formation of free radicals in living organisms. Some occur naturally, such as through the metabolic process, while others are introduced into the body by way of chemical agents, radiation, microbes and viruses.

The initial presence of the free radical initiates a chain reaction in which a number of biomolecules in the organism are oxidized. By oxidizing lipids, for example, these free radicals can affect cell membranes, the permeability of cell membranes, ion channels contained therein, cell function, etc. By oxidizing proteins, for example, free radicals can alter enzymes, muscular function, nerves, etc. And by oxidizing nucleic acids, for example, free radicals can affect DNA, RNA, and consequently their function, regulation, or expression products. Spin trapping agents are utilized to terminate or inhibit this damaging cascade of reactions. It has been found that oxygen-centered free radicals and carbon-, nitrogen-, phosphorous- and sulfur-centered radicals react more readily with the spin trapping agent of the invention than with the potential target biomolecules. The reaction with the spin trapping agent results in the formation of a stable spin adduct and thus, terminates and/or inhibits the damaging chain reaction.

Hence, the azulenyl nitrone compounds of the present invention can be used in a method of treating, alleviating, modulating, or inhibiting the effects in the heart or brain of ischemia or reperfusion injury, acute respiratory distress syndrome (ARDS), sepsis, septic shock and the like. The invention also demonstrates a capacity to preserve organs prior to transplantation comprising contacting the organ to be preserved with an organ preserving effective amount of a compound of the invention.

The phrase "pharmaceutically acceptable salt" includes any type of salt of the azulenyl nitrones of the present invention, whether derived from the addition to the nitrone of a base or an acid, which is suitable for pharmacologic use. Hence, the salt can be obtained by the addition of a alkali or alkaline earth substance (e.g., sodium hydroxide, calcium carbonate, magnesium sulfate and the like) to a nitrone bearing an acidic group (e.g., carboxylic acid or sulfonic acid). Conversely, any free basic functional groups (such as an amino group) on the nitrone can be treated with an acidic substance (e.g., hydrochloric acid, nitric acid and the like) to provide an acid addition salt.

The compounds of the invention can be administered alone or in combination with one or more other biologically active (preferably, therapeutically active) agents, either substantially simultaneously or sequentially. An effective amount of azulenyl nitrone, co-administered with a second agent exhibiting some tissue necrosis or toxicity, may reduce the harmful side effect of the co-administered drug while still deriving the benefit of the therapeutic effect of the second drug. Hence, a combination comprising a therapeutically effective amount of adriamycin, taxol, cis-platin, or other anticancer agents, or AZT, DDI, or other protease inhibitors and an amount of azulenyl nitrone effective to reduce toxicity associated with the other drug(s) is expressly contemplated.

5.5. Other Specific Embodiments and Illustrative Methods

The present invention further contemplates compounds of the formula:

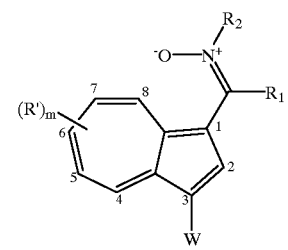

in which $R_1$ may be a hydrogen, a linear or branched alkyl group comprising 1–6 carbon atoms, or an aryl group comprising 6–10 carbon atoms; $R_2$ may be a linear or branched alkyl group comprising 1–6 carbon atoms, or an aryl group comprising 6–10 carbon atoms; R' may be a linear or branched alkyl group comprising 1–6 carbon atoms; W may be a linear or branched alkyl group comprising 1–6 carbon atoms, an aryl group comprising 6–10 carbon atoms, or an electron-withdrawing group; m may be 0, 1, 2, or 3 (if m is 2 or 3, each R' may be the same as or different from one another) or a salt thereof. Specific compounds may, of course, be in the form of its metal salt, such as an alkali or alkaline-earth metal salt, its ammonium or tetraalkylammonium salt. A preferred azulenyl nitrone appears green to the naked eye.

In addition, the invention provides a method of trapping a reactive free radical comprising providing a compound of the general formula:

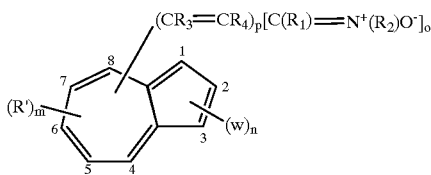

as already defined, above; and allowing the compound to combine with a reactive free radical to provide a spin adduct comprising a combination product of the compound or its salt and a free radical.

In specific embodiments of the invention, the free radical is carbon-centered or is centered on a heteroatom. In particular, the heteroatom is selected from nitrogen, oxygen, phosphorus, or sulfur. The free radical can also be centered on a metal, especially a heavy metal, or more particularly, a transition metal, an actinide metal, or a lanthanide metal. Specific free radicals, which are contemplated to form an adduct with an azulenyl nitrone of the invention include, but are not limited to, singlet oxygen, hydroxyl, superoxide, hydroperoxide, alkylperoxide, or nitric oxide radical. The free radical may also derived from a photosensitizer.

The adduct can undergo further reactions to generate compounds of the formula:

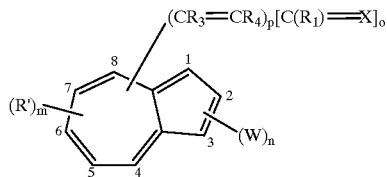

in which R1, R2, R3, R4, R', W, p, n, o and m are as defined previously and X is oxygen, nitrogen, or sulfur.

Yet other methods include a method of detecting oxidation products in a medium comprising combining a compound of the general formula, above, or its salt with a medium and detecting the presence of an adduct or an end-product thereof. Such methods may further comprise the structural characterization of the spin adduct formed or an end-product thereof to obtain information relating to the initial free radical or oxidative species. In the methods, above, the medium may be any solid, liquid, or gaseous medium, but preferably one that comprises a combustible fuel, lubricant, solvent, foodstuff (e.g., meat, poultry, fish, frying oil, vegetable oil), or a biological fluid (e.g., whole blood, peripheral blood, plasma, serum, cerebrospinal fluid, urine, semen, tears, saliva, mucus and the like) or a fraction thereof. The medium may also be a cell culture or a supernatant thereof.

In yet another method, azulenyl nitrone compounds can be used in the screening of natural products that readily give rise to free radicals, e.g., enediyne antibiotics, such as bleomycin, or iron-centered drugs, which may eventually bind DNA/RNA.

Specific compositions include, but are not limited to, a pharmaceutical composition for alleviating a the ill effects of a pathologic condition mediated or initiated by a reactive free radical, in which the composition comprises an effective amount of the compound of the general formula and a pharmaceutically acceptable carrier. Other compositions comprising the compounds of the present invention and a carrier are also contemplated including, but not limited to, those that inhibit oxidation, a fuel additive, a food additive (such as one that is added to a vegetable oil), a cosmetic (such as a facial or body sunscreen of characteristic colors and which change color, indicating overexposure to oxidative conditions or elements). Still other compositions may be those that alleviate the ill effects of aging and in which the carrier is sterile.

Still another objective of the invention is a process for malking an azulenyl nitrone comprising: (a) providing an azulene: (b) introducing a acyl group to the azulene at a position that is to bear a nitrone group; (c) converting the acyl group to a nitrone group to provide an azulenyl nitrone. The process contemplated could further comprise introducing a second acyl group to the azulene at a position that is to bear a group designated W, or it could further comprise converting the second acyl group to a group designated W. Preferably, the group designated W comprises an electron-withdrawing group and that the acyl group comprises an aldehyde. The second acyl group may comprise an acyl halide. Specifically, the group designated W comprises a carboxylic acid, its ester, amide, or salt.

Generally, thus, those additional applications of the present invention lead to a method of alleviating the ill effects of ischemia or reperfusion injury in a subject comprising administering to the subject an effective amount of a compound of the invention, a method of alleviating the ill effects of Acute Respiratory Distress Syndrome (ARDS) in a subject comprising administering to the subject an effective amount of a compound of the invention, or a method of alleviating the ill effects of aging, apoptosis, or senescence in a subject comprising administering to the subject an effective amount of a compound of the invention.

The present invention also contemplates a composition for the treatment of an inflammation in a warm-blooded animal comprising an azulenyl nitrone of the invention a topical carrier. The composition of may come in the form of an aqueous solution, oil, cream, cake, powder, emulsion, or suspension. Moreover, the nitrone may further comprise a group W that is an unsaturated aliphatic group comprising 2–14 carbon atoms. The unsaturated aliphatic group can be further substituted by an electron-withdrawing group, an aryl group comprising 6–18 carbon atoms, a saturated or unsaturated monocyclic or polycyclic ring system comprising 5–20 carbon atoms. Alternatively, the unsaturated aliphatic group may include a substituted or unsubstituted azulene. The group W may simply includes a hydrophilic moiety, such as a beta-lactam. In particular, the group W may include a 2-pyrrolidone group or is a carboxylic acid, 2-(2-pyrrolidon-N-yl)ethyl ester.

Yet another compound of the invention has the general formula

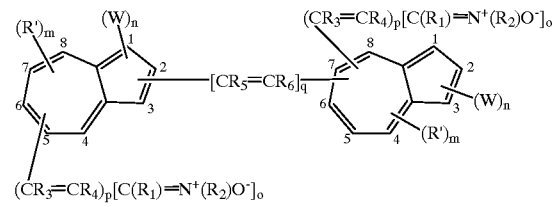

in which $R_1$ may be a hydrogen, a linear or branched alkyl group comprising 1–6 carbon atoms, or an aryl group comprising 6–10 carbon atoms; $R_2$ may be a linear or branched alkyl group comprising 1–6 carbon atoms, or an aryl group comprising 6–10 carbon atoms; $R_3$ may be a hydrogen, or a linear or branched alkyl group comprising 1–6 carbon atoms; $R_4$ may be a hydrogen, or a linear or branched alkyl group comprising 1–6 carbon atoms; $R_5$ may be a hydrogen, or a linear or branched alkyl group comprising 1–6 carbon atoms; $R_6$ may be a hydrogen, or a linear or branched alkyl group comprising 1–6 carbon atoms; R' may be a linear or branched alkyl group comprising 1–6 carbon atoms; W may be a linear or branched alkyl group comprising 1–6 carbon atoms, an aryl group comprising 6–10 carbon atoms, or an electron-withdrawing group; n may be 0, 1, or 2 (if n is 2, each W may be the same as or different from one another); m may be 0, 1, 2, or 3 (if is 2 or 3, each R' may be the same as or different from one another); o may be 1 or 2 (if o is 2, each $R_1$ and $R_2$ may be the same as or different from one another); p may be 0, 1, or 2 (if p is 2, each $R_3$ and $R_4$ may be the same as or different from one another); q may be 0, 1, 2, 3 or 4 (if q is greater than 1, $R_5$ and $R_6$ may be the same as or different from one another) or a salt thereof.

It is hoped that the invention has been described herein in a manner that allows one of ordinary skill ample and adequate disclosure to practice the invention. In an overabundance of caution, however, the following detailed examples are provided further consideration of the interested reader.

6. EXAMPLES
6.1. Preparation of Azulenyl Nitrones
6.1.1. Materials and Methods A number of azulene starting materials are known or commercially available. Azilene, for example, is available from Aldrich Chemical Co. (Cat. No. A9,720-3). Guaiazulene, 7-isopropyl-1,4-dimnethylazulene, is also sold by Aldrich (Cat. No. G1-100-4). Guaiazulene can also be isolated from chamomile oil or guaiac wood oil. Its 3-sulfonic acid, sodium salt, derivative is known as an anti-inflammatory and anti-ulcerative agent. The total synthesis of guaiazulene is described by Plattner et al., in *Helv. Chim. Acta* (1949) 32:2452. The pharmacokinetics of guaiazulene 3-sulfonate sodium salt in animals is described by Mukai, H. et al., in *J. Pharmacobio-Dyn.* (1985) 8:329, 337. The effect of guaiazulene or its salt on gastric and duodenal ulcers in rat models has been described. See, Okabe, S. et al., in *Nippon Yakurigaku Zasshi* (1986) 88:467; Chem. Abstr. (1987) 106:43769.

4,6,8-Trimethylazulene can be purchased from Fluka. Lactarviolin, 7-isopropenyl-4-methyl-1-azulenecarboxaldehyde, is an antibiotic pigment produced by the fungus *Lactarius deliciosus*. Chamazulene, 7-ethyl-1,4-dinethylazulene, is an anti-inflammatory agent that can be obtained from chamazulenogenic compounds found in chamomile, wormwood and yarrow. Chamazulene is a blue oil, but its trinitrobenzene derivative, mp 131.5–132.5 degrees C., provides dark violet needles from absolute ethanol. Other potential starting materials include 4-methyl-1-azulenecarboxaldehyde, a liverwort component and linderazulene, a tricyclic 1,4-dimethylazulene derivative containing a 3'-methylfuranyl ring fused to the 7- and 8-positions (the furan oxygen is attached to the 8-position) of the azulene nucleus. Other potential azulene starting materials are known to those of ordinary skill in the art.

Melting points were determined on a Thomas-Hoover Meltemp apparatus and are uncorrected except where indicated. $^1$H NMR spectra were recorded on a General Electric 300-MHz instrument. Chemical shifts are reported in values (parts per million, ppm) relative to an internal standard of tetramethylsilane in $CDCl_3$, except where noted. Abbreviations used in NMR analysis are as follows: s, singlet; d, doublet; t, triplet; m, multiplet; dt, doublet of triplets. Analytical thin-layer chromatography (TLC) was performed on Baker-flex silica gel 1B2-F plastic plates. Microanalyses were obtained from the Florida International University Microanalytical Laboratory and from Galbraith Laboratories, Inc. Solvents and reagents were used as purchased, except as noted. TEF was distilled from sodium metal/benzophenone ketyl.

6.1.2. General Procedure A

Beginning with a starting azulene, such as guaiazulene, an electron-withdrawing substituent (e.g., a carboxylic acid ester) can be placed on the ring system by the following procedure: To a 0.1M solution of starting azulene in dry $Et_2O$ at rt is added oxalyl bromide (1.0 eq) dropwise over 15 minutes under argon with stirring. The mixture is stirred at rt for 1 hour and then 2 eq of EtOH is added dropwise over 10 minutes. The resulting mixture is stirred an additional hour at rt and is then poured into a separatory final containing $Et_2O$ and sat aq. $NaHCO_3$ solution. The $Et_2O$ layer is washed with $H_2O$, dried over $MgSO_4$ and evaporated to provide the desired product in 80% yield. It is important to note that virtually any nucleophile, other than the EtO$^-$ illustrated here, can be introduced to the carbonyl-containing electron-withdrawing group by allowing the desired nucleophile to react with the acyl bromide intermediate.

6.1.3. Procedure B

A 1-methyl substituent can be oxidized to a carboxaldehyde group by the following procedure: To a stirred mixture of 100 ml of acetonitrile, 5 ml of water and 3.7 mmol of the azulenyl ester of Procedure A at room temperature is added 2,3-dichloro-5,6-dicyano-1,4-benzoquinone (7.8 mmol) in one portion. The reaction mixture is stirred at rt for 60 minutes. The contents of the reaction flask are then poured into 2 liters of $CHCl_3$ and the solution is dried over $MgSO_4$, filtered and concentrated to give a brown solid. This solid is purified by column chromatography on silica gel (elution with $CHCl_3$) to give a red solid. Dissolution of this solid in 250 ml of $Et_2O$ and treatment with 150 ml of sat. aq. sodium thiosulfate solution in a separatory funnel provides, after vigorous shaking, a red ether layer that is subsequently washed with 100 ml of sat. aq. sodium chloride solution. The washed organic solution is dried over anhydrous magnesium sulfate, filtered and concentrated to furnish 2.74 mmol (74%) of the solid red aldehyde.

6.1.4. Procedure C

A carboxaldehdye group is converted readily to, for example, a N-tert-butyl nitrone group, by the following method: To a 0.2M solution of the aldehyde obtained by Procedure B in dry pyridine under argon at rt is added solid N-tert-butylhydroxylamine hydrochloride (1.5–2.0 eq). The mixture is heated with stirring to 95° C. for one hour and then allowed to cool to rt. The pyridine is removed on the rotary evaporator, and the residue is dissolved in $CHCl_3$. The $CHCl_3$ layer is washed with water and dried over $MgSO_4$. Evaporation of the $CHCl_3$ followed by silica gel chromatography of the residue ($CHCl_3$:MeOH) provides the solid green azulenyl nitrone in 96% yield.

6.1.5. Procedure D

A carboxaldehyde group can be introduced, e.g., at the 1-position of azulene by treating the azulene starting material with $POCl_3$ in DMF (the Vilsmeier reaction). See, Hafner, K. and Bernhard, C., in *Angew. Chem.* (1957) 69:533; Treibs et al. *Chem. Ber.* (1959) 92:141. The resulting aldehyde can then be converted to the nitrone by the method of Procedure C.

6.1.6. Procedure E

Likewise, a sulfonate group can be introduced, e.g., at the 3-position, of guaiazulene by treating the starting azulene with $SO_3$ in dioxane, followed by treatment of the resulting sulfonic acid with a base, such as sodium hydroxide. See, Miyazaki, S. et al., in Japanese Patent Publ. No. 3065; Chem. Abstr. (1960) 54:13090.

6.1.7. Procedure F

Two carboxaldehdye groups are converted readily to, for example, N-tert-butyl nitrone groups, by the following method: To a 0.5M solution of the di-aldehyde in dry pyridine under nitrogen at rt is added solid magnesium sulfate (0.1–0.4 eq) and solid N-tert-butylhydroxylamine hydrochloride (2.0–4.0 eq). The mixture is heated with stirring to 95° C. and is stirred overnight. Upon cooling to rt, the reaction mixture is poured into a separator funnel containing 60 ml of $CHCl_3$ and 60 ml of sat aq. $NaHCO_3$. The aqueous layer is separated and washed with three 30 ml portions of $CHCl_3$. The combined organic layers are dried over anhydrous $MgSO_4$, filtered, and evaporated to give the pure desired bis-nitrone.

6.2. Syntheses of Representative Azulenyl Nitrones

Using one or more of the starting materials described above, or any other azulene ring system of interest, numerous azulenyl nitrones can be prepared. Thus, for example, 2,4,6-trimethylazulene can be treated with oxalyl bromide in ether by the method of Procedure A to provide, after the addition of a suitable nucleophile, $Nu^-$, a 3-CONu-substituted 4,6,8-trimethylazulene. Subjecting this intermediate to the conditions of the Vilsmeier reaction (Procedure B), followed by treatment of the resulting carboxaldehyde with N-tert-butylhydroxylamine hydrochloride in pyridine (Procedure C) provides the compound illustrated below:

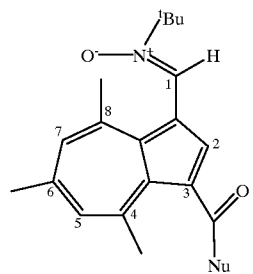

in which the group Nu may be virtually any nucleophilic group, but preferably, hydroxyl, lower alkoxy (e.g., methoxy, ethoxy and the like), N,N'-di(lower alkyl)amide (e.g., diimethylamide, diethylamide and the like), oxo salt, trifluoromethyl, spermine, N-methylglutamine, long chain aliphatic amine (e.g., $C_8$–$C_{22}$ amino), sphingosine, polylysine, an antisense oligonucleotide sequence, a monoclonal antibody (preferably linked via a connecting chain), a DNA intercalator (e.g., an acridine and the like), or a histone.

By following the procedures outline, above, the compounds listed in the Table, below, are prepared.

TABLE

Representative Azulenyl Nitrones

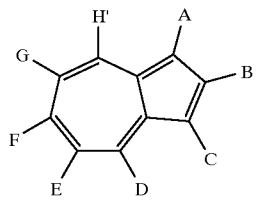

| Compound # | A | B | C | D | E | F | G | H' |
|---|---|---|---|---|---|---|---|---|
| 1 | $CH=N^+(^tBu)O^-$ | H | $CO_2Et$ | $CH_3$ | H | H | $^iPr$ | H |
| 2 | $CH=N^+(^tBu)O^-$ | H | $CONME_2$ | $CH_3$ | H | H | $^iPr$ | H |
| 3 | $CH=N^+(^tBu)O^-$ | H | CHO | $CH_3$ | H | H | $^iPr$ | H |
| 4 | $CH=N^+(^tBu)O^-$ | H | $CO_2^-Na^+$ | $CH_3$ | H | H | $^iPr$ | H |
| 5 | $CH=N^+(^tBu)O^-$ | H | $COCF_3$ | $CH_3$ | H | H | $CMe=CH_2$ | H |
| 6 | $CH=N^+(^tBu)O^-$ | H | CO-spermine | $CH_3$ | H | H | $^iPr$ | H |
| 7 | $CH=N^+(^tBu)O^-$ | H | $CONEt_2$ | $CH_3$ | H | H | $^iPr$ | H |
| 8 | $CH=N^+(^tBu)O^-$ | H | $CON(Me)CH_2(CHOH)_4CH_2OH$ | $CH_3$ | H | H | $^iPr$ | H |
| 9 | $CH=N^+(^tBu)O^-$ | H | $CONH(CH_2)_{17}Me$ | $CH_3$ | H | H | $^iPr$ | H |
| 10 | $CH=N^+(^tBu)O^-$ | H | CONH-sphingosine | $CH_3$ | H | H | $^iPr$ | H |
| 11 | $CH=N^+(^tBu)O^-$ | H | CONH-polylysine | $CH_3$ | H | H | $^iPr$ | H |
| 12 | $CH=N^+(^tBu)O^-$ | H | CONH-antisense | $CH_3$ | H | H | $^iPr$ | H |
| 13 | $CH=N^+(^tBu)O^-$ | H | CONH-mAb | $CH_3$ | H | H | $^iPr$ | H |
| 14 | $CH=N^+(^tBu)O^-$ | H | CONH-acridine | $CH_3$ | H | H | $^iPr$ | H |
| 15 | $CH=N^+(^tBu)O^-$ | H | CONH-histone | $CH_3$ | H | H | $^iPr$ | H |
| 16 | $CH=N^+(^tBu)O^-$ | H | $CH=N^+(^tBu)O^-$ | $CH_3$ | H | H | $^iPr$ | H |
| 17 | $CH=N^+(^tBu)O^-$ | H | H | $CH_3$ | H | H | $CMe=CH_2$ | H |
| 18 | $CH=N^+(^tBu)O^-$ | H | H | H | H | H | H | H |
| 19 | H | H | H | H | H | $CH=N^+(^tBu)O^-$ | H | H |
| 20 | H | H | H | $CH=N^+(^tBu)O^-$ | H | H | H | H |
| 21 | $CH_3$ | H | H | $CH=N^+(^tBu)O^-$ | H | H | $^iPr$ | H |
| 22 | $CH_3$ | H | H | $CH_3$ | H | $CH=N^+(^tBu)O^-$ | $^iPr$ | H |
| 23 | $CPh=N^+(^tBu)O^-$ | H | $CO_2Et$ | $CH_3$ | H | H | $^iPr$ | H |
| 24 | $CH=N^+(^tBu)O^-$ | H | CN | $CH_3$ | H | H | $^iPr$ | H |
| 25 | $CH=N^+(^tBu)O^-$ | H | $SO_2CH_3$ | $CH_3$ | H | H | $^iPr$ | H |
| 26 | $CH=N^+(^tBu)O^-$ | H | $SO_3^-Na^+$ | $CH_3$ | H | H | $^iPr$ | H |
| 27 | $CH=N^+(^tBu)O^-$ | H | $P(O)(OMe)_2$ | $CH_3$ | H | H | $^iPr$ | H |
| 28 | $CH=N^+(^tBu)O^-$ | H | $P(O)(O^-Na^+)_2$ | $CH_3$ | H | H | $^iPr$ | H |
| 29 | $CH=N^+(^tBu)O^-$ | H | $NO_2$ | $CH_3$ | H | H | $^iPr$ | H |

TABLE-continued

Representative Azulenyl Nitrones

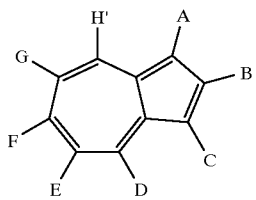

| Compound # | A | B | C | D | E | F | G | H' |
|---|---|---|---|---|---|---|---|---|
| 30 | CH=CHCH=N⁺(ᵗBu)O⁻ | H | CO₂Et | CH₃ | H | H | ⁱPr | H |
| 31 | CH=N⁺(ᵗBu)O⁻ | H | H | CH₃ | H | H | Ac | H |
| 32 | CH=N⁺(Ph)O⁻ | H | CO₂Et | CH₃ | H | H | ⁱPr | H |
| 33 | CH=N⁺(ᵗBu)O⁻ | H | H | CH₃ | H | H | ⁱPr | H |
| 34 | CH=N⁺(ᵗBu)O⁻ | H | CH=N⁺(ᵗBu)O⁻ | H | H | H | H | H |

In particular, the following synthetic steps may be employed:

Compound #1 Starting with guaiazulene, use Procedure A, then B, then C.

Compound #2 Procedure A (substitute 2 eq. of HNMe₂ for EtOH), then B, then C.

Compound #3 Vilsmeier formulation of guaiazulene according to Procedure D, then B, then C.

Compound #4 Procedure A (substitute NaOH for EtOH), then B, then C.

Compound #5 Protect aldehyde of lactaroviolin as dimethyl acetal (benzene, MeOH, cat. para-toluenesulfonic acid), then trifuoroacetylate With (F₃CCO)₂O, ether, rt [Ref: Anderson, A. J., Jr. et al., in *J. Org. Chem.* (1965) 30:131], H₃O⁺ hydrolysis of acetal, then C.

Compound #6 Procedure A (substitute 2 eq. [NB: 2d equiv scavenges HCl] spermine for EtOH), then B, then C [NB: reaction proceeds on 1° amino group of spermine].

Compound #7 Procedure A (substitute 2 eq. HNEt₂ for EtOH), then B, then C.

Compound #8 Procedure A (substitute 2 eq. N-Methyl glucamine for EtOH), then B, the C.

Compound #9 Procedure A (substitute 2 eq. octadecyl-amine for EtOH), then B, then C.

Compound #10 Procedure A (substitute 2 eq. sphingosine for EtOH), the B, then C.

Compound #11 Procedure A (substitute polylysine for EtOH), then B, then C.

Compound #12 Procedure A (substitute an antisense oligonucleotide, like poly(dG)₁₀, for EtOH), then B, then C.

Compound #13 Procedure A (substitute a monoclonal antibody [NB: any monoclonal Ab listed in ATCC Catalog,, for instance] for EtOH), then B, then C.

Compound #14 Procedure A (substitute H₂N(CH₂)₃NH [acridine] for EtOH), then B, then C [Ref: Plouvier, B. et al., in *Bioconjugate Chemistry* (1994) 5:475 (acridine bioconjugates)].

Compound #15 Procedure A (substitute a histone [NB: e.g., histone type-II AS from calf thymus, available from Sigma] for EtOH), then B, then C.

Compound #16 Vilsmeier formylation of guaiazulene according to Procedure D, then C with ≧2 eq. tert-butylNHOH·HCl.

Compound #17 Procedure C starting with lactaroviolin.

Compound #18 Procedure C with ≧2 eq. tert-butylNHOH·HCl starting with 1-azulenecarboxaldehyde [NB: this starting material is obtained readily by a Vilsmeier reaction involving azulene, according to Procedure D].

Compound #19 Starting with 6-azulenecarboxaldehyde [Ref. Huenig, S. et al., in *Liebigs Ann. Chem.* (1986) 1222 (synthesis 6-azulenecarboxaldehyde and 4-azulenecarboxaldehyde)], obtain nitrone by Procedure C.

Compound #20 Starting with 4-azulenecarboxaldehyde, obtain nitrone by Procedure C.

Compound #21 Metalate guaiazulene by deprotonation at C-4 thyl group using NaNCH₃Ph [Ref: Kurokawa, S., in *Bull. Chem. Soc. Jpn.* (1979) 1748 (metalation of guaiazulene at C-4 methyl group)], then quench resulting organosodium species with Cl(PO)(OMe)₂, metalate resulting phosphonate with LDA/THF and perform Horner Wadsworth Emmons olefination with acetone, subsequent ozonolysis of double bond to give aldehyde, then C.

Compound #22 Same as for Compound #19 substituting guaiazulene for azulene.

Compound #23 This compound is produced by disproportionation of the nitroxide formed when Compound #1 captures a phenyl radical under conditions of the Gokel-modified Gomberg-Bachmann reaction: Compound #1 (100 mM in benzene) is exposed to 1 eq. of Ph-N₂ BF₄, 2 eq. KOAc, and 5 mol%, 18-crown-6 at rt for 1.5 hours [Ref: Gokel, G. W. et al., in *J. Org. Chem.* (1984) 49:1594]. Workup involves evaporation solvent and purification by prep TLC (1:1 EtoAc:Hex). Compound #23 is green.

Compound #24 Cyanation of guaiazulene [Ref: Kitahara, Y. and Kato, T., in *Bull. Chem. Soc. Jpn.* (1964) 37:859], then B, then C.

Compound #25 Treat guaiazulene with AlCl₃, ClSO₂CH₃, CH₂Cl₂, rt [Ref: Repogle, L. L. et al., in *J. Org. Chem.* (1967) 21:1909 (3-azulenylsulfones)], then B, then C.

Compound #26 Sulfonation of guaiazulene according to Procedure E, then B, then A.

Compound #27 Treat guaiazulene with AlCl₃, Cl(PO)(OMe)₂, CH₂Cl₂, rt, then B, then C.

Compound #28 Same as Compound #27 except hydrolyze with NaOH before subjecting to Procedure B.

Compound #29 Catalytic hydrogenation of lactaroviolin, then nitration with HNO₃/H₂SO₄ at 0° C. in AcOH, then Procedure C.

Compound #30 Wittig reaction of Compound #1 with $Ph_3P=CHCHO$, then Procedure C.

Compound #31 Ozonolysis of lactaroviolin, then Procedure C.

Compound #32 Same as for Compound #1 substituting PhNHOH·HCl for tert-butylNHOH·HCl in Procedure C.

Compound #33 Catalytic hydrogenation of lactaroviolin, then Procedure C.

Compound #34 Starting with 1,3-Azulenedicarboxaldehyde [Ref: Hafner, K. and Bernhard, C., *Annalen* (1959) 625:108] obtain bis-nitrone by Procedure F.

Compound #35 Starting with 1,2-bis(guaiazulenylethylene, use Procedure A, then B, then C.

6.3. Detection, Quenching and Characterization of Paramagnetic and Diamagnetic Species

6.3.1. Electron Spin Resonance Spectroscopy

The chromogenic azulenyl nitrones of the present invention facilitate the detection of free radical species by providing a calorimetric indication of adduct formation. For example, the azulenyl nitrone of Compound #1 is green, whereas the diamagnetic and paramagnetic spin adducts with carbon-centered radicals are violet. Paramagnetic species are detectable by ESR, as well. Isolation of the spin adduct can be facilitated by viewing colored bands chromatographic plates indicating the position of each chromophore, even when the chromophore is a diamagnetic combination, disproportionation, or reduction product of the initially formed nitroxides.

Compound #1 (100 mM in benzene) is exposed to 1 equiv of the azo compound, $(CH_3)_2CHCH_2(CH_3)C(CN)N=N(CN)C(CH_3)CH_2CH(CH_3)_2$, AMVN, and heated to 75° C. for 20 minutes. After cooling to room temperature, the solution is transferred to an ESR tube, and examined by ESR spectroscopy. The ESR spectrum observed is shown FIGS. 1A and 1B. The contents of the ESR tube are applied to a prep TLC plate ($SiO_2$) and eluted with 99:1 (v/v) $CHCl_3$:MeOH. The violet band is scraped from the plate and the $SiO_2$ extracted with 99:1 (v/v) $CHCl_3$:MeOH. The solution is evaporated to dryness and the residue is dissolved in 100 μl of benzene and transferred to a clean ESR tube. The ESR spectrum observed is identical to that recorded previously, indicating that the isolated violet product is responsible for the prior ESR signal.

Similarly, chromatographic separation of the highly colored diamagnetic spin adducts can also be accomplished.

6.3.2. Chromogenic Assays

Compound #1 (10 mg) is dissolved in 50 ml of corn oil and the resulting green oil is maintained at room temperature under aerobic conditions for four to seven months. During this time, the color of the solution changes from green to yellow to red, reflecting the progressive, increasing rancidity of the oil. It is noted that Compound #1, when added to continuously aerated chlorobenzene (a solvent that contains no readily oxidizable groups, unlike vegetable oil), remains unchanged over time.

6.4. Diagnostic, Prophylactic, or Therapeutic Applications

6.4.1. Prolongation of the Life Span of the Senescence Accelerated Mouse (SAM-P8)

SAM-P8 mice are available from Prof. Toshio Takeda (Kyoto University, Japan). The mice are housed under standard conditions at 25° C. with a 12-hour light/dark cycle and allowed free access to water and a standard diet. At 3 months of age, they were divided into four groups: two groups (12 male and 12 female mice) are used as control, and two groups are designated the experimental groups (13 male and 12 female mice). The experimental groups are given an azulenyl nitrone (either Compound 4 or 26, 30 mg/kg, i.p.) daily and their body weight is measured. The control groups are sham injected with saline.

At the end of the study, it is observed that the azulenyl nitrones of the present invention prolong the life span of SAM-P8 mice significantly (i.e., by about 20–30%).

6.4.2. Delay of Senescence in Human Diploid Fibroblast Cells

IM-90 cells are obtained from the Coriell Institute for Medical Research at population doubling level (PDL) 10.85. The population doublings (PDs) are calculated as $\log_2(D/D_0)$, where D is the density of cells when harvesting and $D_0$ is the density of cells when seeding. The stock cultures are split weekly and grown in 100-mm Corning tissue culture dishes containing 10 ml of Delbecco's modified Eagle's medium (DMEM) supplemented with 10% (vol/vol) dialyzed fetal bovine serum (Sigma).

To test the effect of ambient oxygen on the life span, cells are cultured in 25-$cm^2$ Corning flasks with 5 ml of medium. Early-passage cells are seeded at $0.1–0.3\times10^6$ cells per flask and late-passage cells are seeded at $0.5\times10^6$ cells per flask. The flasks are gassed with a mixture of 3% $O_2$/5% $CO_2$/92% $N_2$ or with a mixture of 20% $O_2$/5% $CO_2$/75% $N_2$ for 30 sec, then plug-sealed, and incubated at 37° C. The cultures are split after the cells reached confluence. Early-passage cells usually reach confluence in 5 or 6 days, and late-passage cells, even with increased seeding density, reach saturation density in 10–14 days. At senescence, cells have not doubled for at least 21 days.

To determine the effect of azulenyl nitrone on the replicative life span of cells, Compound 26 (stock - 50 mM in phosphate-buffered saline) is added to culture medium at a final concentration of 200–1200 μM after each splitting. If cells are not split on day 7, the cells are fed with fresh medium containing Compound 26.

It is found that Compound 26 not only delays the onset of senescence, relative to untreated cells, but the azulenyl nitrone also rejuvenates near senescent cells in a dose-dependent manner.

6.4.3. Improvement of Cognitive Performance of Sprague-Dawley Rats

Forty male Sprague-Dawley Rats (aged 24-month-old) are divided into five groups of 8 rats each. Three groups are treated over a period of 3–5 months with daily intraperitoneal (ip) injections of azulenyl nitrone 4 at different dosages (5 mg/kg, 15 mg/kg and 30 mg/kg) in saline. A fourth group is treated with 15 mg/kg of the azulenyl nitrone for a period of 20 days only. The fifth group is treated with saline only and serves as a control.

One month after the stated treatment period, each group is tested in a Morris water maze. The rats are scored for their rates of acquisition (i.e., learning), memory retention, passive avoidance behavior, motor activity, motor skill and any differences in their basal levels of brain lipid peroxidation. The latter may be gauged by TBAR formation. It is found that, compared to the control group and the group treated for 20 days only, the rats in the groups receiving 5, 15 and 30 mg/kg of azulenyl nitrone 4 for at least three months exhibit better cognitive performance in terms of acquisition and memory retention, and are further found after 5 months of chronic treatment to have reduced levels of brain lipid peroxidation.

This result demonstrates the effectiveness of an azulenyl nitrone of the present invention to inhibit the negative effects of free radical-based aging on brain function and physiology.

6.4.4. Reduction in Multiple Organ Dysfunction and Cytokine Secretion

A saline solution of lipo-polysaccharide is administered to 16 male Sprague-Dawley Rats to induce organ dysfunction and the secretion of a variety of cytokines, including tumor necrosis factor-alpha (TNF-alpha), interleukin-1 alpha (IL-1 alpha) and interleukin-1 beta (IL-1 beta). Thirty to forty-five minutes prior to LPS administration, half of the rats are treated with intraperitoneal injections of azulenyl nitrone 1 at varying dosages (5–100 mg/kg). Several markers are monitored, including serum levels of aspartate aminotransferase (AST) and alanine aminotransferase (ALT). The levels of AST and ALT are taken as indicators of LPs-induced liver damage. Also monitored are serum levels of urea and creatinine, which indicate kidney damage induced by LPS.

It is found that a dose-dependent reduction in these liver and kidney damage markers can be correlated to azulenyl nitrone administration. It is also discovered that azulenyl nitrone 1 is able to prevent (i.e., serve as a prophylatic against) LPS-induced pulmonary edema. This nitrone also exhibits some inhibition of both thrombocytopenia and leukopenia. Moreover, marked decreases in serum levels of LPS-stimulated TNF-alpha, IL-1 alpha and IL-1 beta are observed.

6.4.5. Inhibition of Oxidative Modification of Cholesterol and Triglycerides of LDL Albumin-free LDL is dialyzed against a buffer containing 50 mM borate at pH 9.0. Alternatively, a buffer containing 0.15M NaCl/5 mM Tris/1 mM $CaCl_2$/0.1 mM EDTA at pH 7.4 can also be used. Dialysis is carried out under an atmosphere of nitrogen at 4 degrees C. over a 48 h period, with up to six changes of buffer. Dialyzed LDL (0.5 mg protein/ml) is incubated with bee venom phospholipase $A_2$ ($PLA_2$, 3.3 units/ml) at 37 degrees C. After 2 h, 26,000 units/ml of Soybean LO (SLO, type V, Sigma, St. Louis, Mo.) is added. Incubation is then continued with gentle shaking at 37 degrees C. under an ambient atmosphere.

To determine baseline levels of oxidative modification of LDL in the absence of azulenyl nitrone, aliquots are taken at predetermined time intervals over a 24 h period. Protein can be determined by the method of Lowry, H. O. et al., in *J. Biol. Chem.* (1951) 193:265 and the neutral lipid profile can be obtained by the method of Kuksis, A. et al., in *J. Chromatogr. Sci.* (1975)13:423.

The effect of azulenyl nitrone is examined by the addition of azulenyl nitrone to the incubation mixture comprising LDL/$PLA_2$ at time 0 h at varying final concentrations (0, 0.5, 1.0, 2.0, 5.0 and 10.0 mM). Incubation is then continued at 37 degrees C. for 2 h, followed by the addition of SLO. After 2 h, the reaction is quenched by cooling the incubation tubes in ice water and the addition of 3 mM EDTA/0.05% (w/v) reduced glutathione under an argon atmosphere.

The results indicate that azulenyl compounds of the present invention inhibit the oxidation of cholesteryl esters and triglycerides of LDL in a concentration-dependent, though not necessarily linear, manner.

The foregoing examples of preferred embodiments are provided simply to illustrate the present invention. Other embodiments of the present invention are apparent to one of ordinary skill in the art and are considered to fall within the scope and spirit of the present invention. Hence, the examples are not to be construed to limit the invention in any way, which invention is limited solely by the claims that follow.

6.4.6. In Vivo Diagnostic Applications

The ability of azulenyl nitrones to cross the blood brain barrier is determined by administering to a rodent the nitrone in a lipid (e.g., lecithin, liposome, lipofectin, or lipofectamine) mixture and analyzing the blood and brains for nitrone and/or aldehyde. As an example, mice are dosed at about 15 mg/kg iv with azulenyl nitrone 1 in a liposome-based mixture at a concentration of 1.5 mg/ml. Blood is sampled and the brains are perfused with saline. Afterward, the brains are removed. The azulenyl nitrone 1 is extracted from the blood plasma and brain tissue and measured. It is demonstrated that a higher concentration of azulenyl nitrone is found in the brains of the mice than in their plasma and further demonstrates that 1 is able to cross the blood brain barrier and is absorbed by brain tissue.

Furthermore, it is shown that when an ischemic event is induced in rodents a higher concentration of aldehyde by-product is detectable in the brains of the rodents. As an example, several test and sham gerbils are intraperitoneally (ip) injected with azulenyl nitrone 1 at 100 mg/kg in a liposome-based solution. Thirty minutes after injection, a bilateral carotid occlusion (BCO) is induced on the test gerbils with subsequent reperfusion. Measurements of the ratio of aldehyde to nitrone in the hippocampus of the gerbils show a higher ratio for the BCO treated test-gerbils. It is expected that the BCO treated gerbils would generated free radical species in their hippocampus due to the ischemic event. A higher concentration of azulenyl aldehyde product is consistent with the mechanism of azulenyl nitrone free radical trapping and demonstrates the utility of these nitrones. Furthermore, it is shown that the aldehyde product thus generated is predominately isolated to the region of free radical formation, namely the brain tissue. No substantial amount of azalenyl aldehyde product is observed in the blood.

6.4.7. In Vivo Neuroprotection

In this model the carotid arteries of gerbils are constricted surgically and after a predetermined period, the constriction is removed causing reperfusion and consequently the formation of oxygen free radicals. The test gerbils are dosed intraperitoneally at 100 mg/kg with azulenyl nitrone 1 some time prior to the constriction and 100 mg/kg intraperitoneally some time after the constriction. After several days of reperfusion, the hippocampal cells of the test and sham gerbils are counted. As is expected, an 80% loss of cell viability is observed for the sham gerbils, however, about twice as many viable cells are found for the azulenyl nitrone administered gerbils. Thus, the invention serves as a neuroprotectant and reduces the infarct volume resulting from the ischemia and/or reperfusion.

6.4.8. Anti-Inflammation Topical Treatment

These compositions are in the form of a solution, a cream, a powder, gel, ointrnent, or lotion. They also constitute makeup or makeover products or dermatological cakes containing the ingredients standard to these types of compositions.

| A cream is prepared as follows: | |
| --- | --- |
| azulenyl nitrone 34 | 1 to 0.25 g. |
| Titanium oxide | 10 g. |
| Red iron oxide | 0.3 g. |
| Yellow iron oxide | 0.2 g. |
| Brown iron oxide | 0.4 g. |
| Chestnut iron oxide | 0.2 g. |

Several stearyl alcohols oxyethylenated with 33 mols. of:

| | |
| --- | --- |
| Ethylene oxide | 7 g. |
| Propyl parahydroxybenzoate | 0.2 g. |
| Polyglycol stearate | 6 g. |
| Water, Q.S.P. | 100 g. |

Other creams identical to that described immediately above are prepared by replacing azulenyl nitrone 34 with any of the previously mentioned nitrone compounds.

A dermatological cleansing cake is prepared by mixing together the following components:

| | |
|---|---|
| Esters of sodium isothionate and coprafatty acids (sold under the tradename "IGEPON A" having the formula R—COO—CH2—CH2—SO3—Na, wherein R equals fatty acid derivatives having 12–15 carbon atoms) | 75 g. |
| Lanolin derivatives | 22.75 g. |
| azulenyl nitrone 4(1, acid Na salt) | 0.75 g. |

Other dermatological cleansing cakes, identical to the above, are prepared by replacing azulenylnitrone 4 (1, acid Na salt) with any one of the aforementioned active compounds.

A powder comprising the following mixture:

| | |
|---|---|
| Talc | 99.6 g. |
| Glycerine oleate | 3.0 g. |
| Isopropyl myristate | 7.0 g. |
| azulenyl nitrone 1 | 0.5 g. |
| Perfume | 2 cc. |

Other equally effective powder compositions identical to the above are prepared except that the active ingredient azulenyl nitrone 1 is replaced by any of the other aforementioned active compounds.

A cream is made by dispersing 0.5 g of azulenyl nitrone 1 or 0.2 g of 34 in 30.0 g of propylene glycol. The mixture is then homogenized into 97.4 grams of finished cream, ointment or lotion following a modification of any one of the procedures described in F. W. Martin et al, "Remington's Pharmaceutical Sciences", 14th Ed, Mack Publishing Co., Easton, Pa. 1965.

6.5. Other Indications

The azulenyl nitrones of the present invention find htrther use in the treatment of a variety of other ailments and conditions that are mediated by the inappropriate action of free radicals, including but not limited to oxidative tissue damage, CNS spinal column damage and ophthalmic disorders, progressive neuronal disorders, acute CNS oxidation in stroke, gradual CNS oxidation, migraines, gastric ulceration, ulcers, certain aspects of diarrhea, gastritis, esophagitis, ileitis, ATP depletion in tissue, peripheral organ disease (such as atherosclerosis, bedsores, wounds and muscle overextension), shock, memory disorders, including short term memory loss. The compounds of the invention can also be. useful as analgesics, in particular, as a non-steroidal anti-inflammatory drug (or NSAID). For further information on the indications listed above, the interested reader is referred to U.S. Pat. Nos. Re 35112, 5,025,032, 5,508,305, 5,488,148, 5,036,097, 5,475,032, 5,292,746 and 5,405,874, the disclosures of each of which are incorporated by reference herein.

What is claimed is:

1. A compound of the formula:

$$\text{(R')}_m\underset{5}{\overset{7}{\bigcirc}}\underset{4}{\overset{8}{\bigcirc}}\underset{3}{\overset{1}{\bigcirc}}\overset{(CR_3=CR_4)_p[C(R_1)=N^+(R_2)O^-]_o}{\underset{(W)_n}{}}$$

in which

R$_1$ may be a hydrogen, a linear or branched alkyl group comprising 1–6 carbon atoms, or an aryl group comprising 6–10 carbon atoms;

R$_2$ may be a linear or branched alkyl group comprising 1–6 carbon atoms, or an aryl group comprising 6–10 carbon atoms;

R$_3$ may be a hydrogen, or a linear or branched alkyl group comprising 1–6 carbon atoms;

R$_4$ may be a hydrogen, or a linear or branched alkyl group comprising 1–6 carbon atoms;

R' may be a linear or branched alkyl group comprising 1–6 carbon atoms;

W may be a linear or branched alkyl group comprising 1–6 carbon atoms, an aryl group comprising 6–10 carbon atoms, or an electron-withdrawing group;

n may be 0, 1, or 2 (if n is 2, each W may be the same as or different from one another);

m may be 0, 1, 2, or 3 (if m is 2 or 3, each R' may be the same as or different from one another);

o may be 1 or 2 (if o is 2, each R$_1$ and R$_2$ may be the same as or different from one another);

p may be 0, 1, or 2 (if p is 2, each R$_3$ and R$_4$ may be the same as or different from one another) or a salt thereof.

2. The compound of claim 1 in which p is 0.

3. The compound of claim 1 in which n is 1.

4. The compound of claim 1 in which m is 1 or 2.

5. The compound of claim 1 in which the groups R$_1$, R$_3$, and R$_4$ are all hydrogen.

6. The compound of claim 4 in which at least one R' is a methyl group.

7. The compound of claim 4 in which at least one R' is an ethyl or isopropyl group.

8. The compound of claim 1 in which the group R$_2$ is a tert-butyl group.

9. The compound of claim 1 in which W is an electron-withdrawing group.

10. The compound of claim 1 in which the group (CHR$_3$=CR$_4$)$_p$C(R$_1$)=N$^+$(R$_2$)O$^-$ is at the 1-position when the group W is at the 3-position.

11. The compound of claim 10 in which m is 2 and the groups R' are at the 4- and 7-positions.

12. The compound of claim 9 in which the group W may be a carboxylic acid, carboxylic acid ester, sulfonic acid, sulfonic acid ester, ketone, halogen, cyano, nitro, nitroso, aldehyde, phosphoric acid, phosphoric acid ester, sulfoxide, sulfone, or a salt thereof.

13. The compound of claim 12 in which the group W is a trifluoroacetyl group.

14. The compound of claim 1 in which o is 1.

15. The compound of claim 1 which is 2-methyl[1-(3-carboxylic acid-7-isopropyl-4-methyl)azulenylmethylene]-2-propanamine N-oxide, its ester, amide, or salt.

16. The compound of claim 1 which is 2-methyl[1-(3-carboethoxy-7-isopropyl-4-methyl)azulenylmethylene]-2-propanamine N-oxide.

17. The compound of claim 1 which is 2-methyl[1-(3-sulfonic acid-7-isopropyl-4-methyl)azulenylmethylene]-2-propanamine N-oxide, its ester, amide, or salt.

18. The compound of claim 1 which is 2-methyl[1-(3-methylsulfonyl-7-isopropyl-4-methyl)azulenylmethylene]-2-propanamine N-oxide.

19. A compound of the formula:

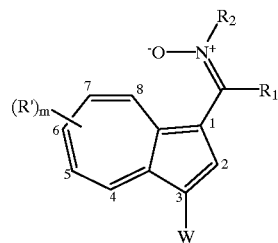

in which
R$_1$ may be a hydrogen, a linear or branched alkyl group comprising 1–6 carbon atoms, or an aryl group comprising 6–10 carbon atoms;
R$_2$ may be a linear or branched alkyl group comprising 1–6 carbon atoms, or an aryl group comprising 6–10 carbon atoms;
R' may be a linear or branched alkyl group comprising 1–6 carbon atoms;
W may be a linear or branched alkyl group comprising 1–6 carbon atoms, an aryl group comprising 6–10 carbon atoms, or an electron-withdrawing group;
m may be 0, 1, 2, or 3 (if m is 2 or 3, each R' may be the same as or different from one another) or a salt thereof.

20. The compound of claim 19 in the form of its metal salt.

21. The compound of claim 20 in which said metal salt is an alkali or alkaline-earth metal salt.

22. The compound of claim 19 in the form of its ammonium or tetraalkylammonium salt.

23. The compound of claim 19 which appears green to the naked eye.

24. The compound of claim 1 which is 1,3-bis(2-methyl-2-propanamine N-oxide)azulenyldimethylene.

25. The compound of claim 1 which is 1,3-bis(2-methyl-2-propanamine N-oxide)-7-isopropyl-4-methylazulenyldimethylene.

26. A pharmaceutical composition for alleviating the ill effects of a pathologic condition mediated or initiated by a reactive free radical, said composition comprising an effective amount of the compound of claim 19 and a pharmaceutically acceptable carrier.

27. A composition comprising a compound of the formula:

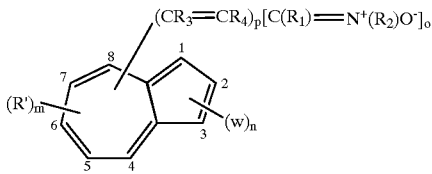

in which
R$_1$ may be a hydrogen, a linear or branched alkyl group comprising 1–6 carbon atoms, or an aryl group comprising 6–10 carbon atoms;
R$_2$ may be a linear or branched alkyl group comprising 1–6 carbon atoms, or an aryl group comprising 6–10 carbon atoms;
R$_3$ may be a hydrogen, or a linear or branched alkyl group comprising 1–6 carbon atoms;
R$_4$ may be a hydrogen, or a linear or branched alkyl group comprising 1–6 carbon atoms;
R' may be a linear or branched alkyl group comprising 1–6 carbon atoms;
W may be a linear or branched alkyl group comprising 1–6 carbon atoms, an aryl group comprising 6–10 carbon atoms, or an electron-withdrawing group;
n may be 0, 1, or 2 (if n is 2, each W may be the same as or different from one another);
m may be 0, 1, 2, or 3 (if m is 2 or 3, each R' may be the same as or different from one another);
o may be 1 or 2 (if o is 2, each R$_1$ and R$_2$ may be the same as or different from one another);
p may be 0, 1, or 2 (if p is 2, each R$_3$ and R$_4$ may be the same as or different from one another) or a salt thereof; and a carrier.

28. A process for making an azulenyl nitrone comprising:
(a) providing an azulene;
(b) introducing a an acyl group to said azulene at a position that is to bear a nitrone group;
(c) converting said acyl group to a nitrone group to provide an azulenyl nitrone.

29. A compound of formula

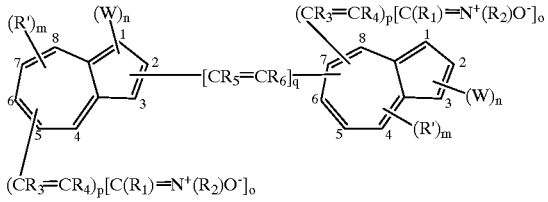

in which
R$_1$ may be a hydrogen, a linear or branched alkyl group comprising 1–6 carbon atoms, or an aryl group comprising 6–10 carbon atoms;
R$_2$ may be a linear or branched alkyl group comprising 1–6 carbon atoms, or an aryl group comprising 6–10 carbon atoms;
R$_3$ may be a hydrogen, or a linear or branched alkyl group comprising 1–6 carbon atoms;
R$_4$ may be a hydrogen, or a linear or branched alkyl group comprising 1–6 carbon atoms;
R$_5$ may be a hydrogen, or a linear or branched alkyl group comprising 1–6 carbon atoms;
R$_6$ may be a hydrogen, or a linear or branched alkyl group comprising 1–6 carbon atoms;
R' may be a linear or branched alkyl group comprising 1–6 carbon atoms;
W may be a linear or branched alkyl group comprising 1–6 carbon atoms, an aryl group comprising 6–10 carbon atoms, or an electron-withdrawing group;
n may be 0, 1, or 2 (if n is 2, each W may be the same as or different from one another);
m may be 0, 1, 2, or 3 (if m is 2 or 3, each R' may be the same as or different from one another);
o may be 1 or 2 (if o is 2, each R$_1$ and R$_2$ may be the same as or different from one another);
p may be 0, 1, or 2 (if p is 2, each R$_3$ and R$_4$ may be the same as or different from one another);
q may be 0, 1, 2, 3 or 4 (if q is greater than 1, R$_5$ and R$_6$ may be the same as or different from one another) or a salt thereof.

30. A method of alleviating the ill effects of ischemia or reperfusion injury in a subject comprising administering to said subject an effective amount of a compound of claim 1 or 19.

31. A method of alleviating the ill efrects of Acute Respiratory Distress Syndrome (ARDS) in a subject comprising administering to said subject an effective amount of the compound of claim 1 or 19.

32. A method of alleviating the ill effects of aging or senescence in a subject comprising administering to said subject an effective amount of the compound of claim 1 or claim 19.

* * * * *